United States Patent
Beech, Jr. et al.

(10) Patent No.: US 7,214,843 B2
(45) Date of Patent: *May 8, 2007

(54) TREATING OXYGENATE CONTAINING FEEDSTREAMS IN THE CONVERSION OF OXYGENATES TO OLEFINS

(75) Inventors: James H. Beech, Jr., Kingwood, TX (US); Cor. F. Van Egmond, Pasadena, TX (US); Ronald G. Searle, Houston, TX (US); Michael Peter Nicoletti, Houston, TX (US); David Ritchie Lumgair, Jr., Craddockville, VA (US)

(73) Assignee: Exxon Mobil Chemical Patents Inc., Houston, TX (US)

(*) Notice: Subject to any disclaimer, the term of this patent is extended or adjusted under 35 U.S.C. 154(b) by 385 days.

This patent is subject to a terminal disclaimer.

(21) Appl. No.: 10/686,461

(22) Filed: Oct. 14, 2003

(65) Prior Publication Data

US 2004/0102670 A1  May 27, 2004

Related U.S. Application Data

(63) Continuation-in-part of application No. 10/421,012, filed on Apr. 22, 2003, now Pat. No. 7,074,979, and a continuation-in-part of application No. 10/304,328, filed on Nov. 26, 2002, now Pat. No. 6,846,966.

(60) Provisional application No. 60/437,698, filed on Dec. 31, 2002.

(51) Int. Cl.
*C07C 1/00* (2006.01)

(52) U.S. Cl. ............ 585/640; 585/638; 585/639
(58) Field of Classification Search ......... 585/638–640
See application file for complete search history.

(56) References Cited

U.S. PATENT DOCUMENTS

| | | | |
|---|---|---|---|
| 2,877,747 A | 3/1959 | Happell | 122/435 |
| 3,781,407 A | 12/1973 | Kamijo et al. | 423/242 |

(Continued)

FOREIGN PATENT DOCUMENTS

JP      05 310181      11/1993

(Continued)

OTHER PUBLICATIONS

Germanischer Lloyd, , "Part I Seagoing Ships", Rules for Classification and Construction, vol. 1, Ship Technology, pp. 1-76, Hamburg, Germany (1998).

(Continued)

*Primary Examiner*—Glenn Caldarola
*Assistant Examiner*—In Suk Bullock

(57) ABSTRACT

This invention is directed to removing contaminants from an oxygenate-containing feedstream for an oxygenate to olefin reaction system. Oxygenate feeds used in the conversion of oxygenates to olefins, and which contain contaminants, are heated to form a vapor stream and a liquid stream. The heating is conducted so that a majority of the metalloaluminophosphate molecular sieve catalyst contaminants is contained in the liquid stream. The vapor stream is separated from the liquid stream, and the separated vapor stream is contacted with the metalloaluminophosphate molecular sieve catalyst to form olefin product. The heating of the feedstream and the separation of the vapor stream can be carried out in one or more stages.

76 Claims, 2 Drawing Sheets

U.S. PATENT DOCUMENTS

| | | | |
|---|---|---|---|
| 3,945,944 A | 3/1976 | Kang | 252/455 |
| 4,042,488 A | 8/1977 | Perciful | |
| 4,083,888 A | 4/1978 | Caesar et al. | 200/682 |
| 4,098,412 A | 7/1978 | Shakshober | 214/15 D |
| 4,163,455 A | 8/1979 | Hebert et al. | 134/167 R |
| 4,293,729 A | 10/1981 | Kolb et al. | |
| 4,371,718 A | 2/1983 | Hutson, Jr. | |
| 4,433,189 A | 2/1984 | Young | 585/640 |
| 4,503,281 A | 3/1985 | Hoelderich et al. | 585/640 |
| 4,665,249 A | 5/1987 | Mao et al. | 585/408 |
| 4,777,321 A | 10/1988 | Harandi et al. | 585/640 |
| 4,814,535 A | 3/1989 | Yurchak | 585/408 |
| 4,814,536 A | 3/1989 | Yurchak | 585/408 |
| 4,826,662 A | 5/1989 | Mao et al. | 422/190 |
| 4,857,667 A | 8/1989 | Harandi et al. | 585/403 |
| 5,028,400 A | 7/1991 | Harandi et al. | 422/211 |
| 5,041,690 A | 8/1991 | Harandi et al. | 568/697 |
| 5,059,738 A | 10/1991 | Beech, Jr. et al. | 585/469 |
| 5,166,455 A | 11/1992 | Chin et al. | 568/697 |
| 5,167,937 A | 12/1992 | Harandi et al. | 422/190 |
| 5,189,975 A | 3/1993 | Zednik et al. | 114/74 |
| 5,313,006 A | 5/1994 | Knifton | 568/698 |
| 5,335,615 A | 8/1994 | Bjorkman | 114/74 R |
| 5,398,629 A | 3/1995 | Wasenius | 114/74 R |
| 5,435,436 A | 7/1995 | Manley et al. | |
| 5,491,273 A | 2/1996 | Santiesteban et al. | 585/639 |
| 5,638,845 A | 6/1997 | Oliver et al. | 134/167 R |
| 5,714,662 A | 2/1998 | Vora et al. | 585/640 |
| 5,899,162 A | 5/1999 | Beaupreet et al. | 114/74 A |
| 6,021,848 A | 2/2000 | Breivik et al. | 166/344 |
| 6,041,726 A | 3/2000 | Filek | 114/74 R |
| 6,121,504 A | 9/2000 | Kuechler et al. | 585/640 |
| 6,166,282 A | 12/2000 | Miller | 585/638 |
| 6,482,998 B1 | 11/2002 | Kuechler et al. | 585/638 |
| 6,486,219 B1 * | 11/2002 | Janda et al. | 518/706 |
| 6,846,966 B2 * | 1/2005 | Lumgair et al. | 585/639 |
| 6,899,046 B2 | 5/2005 | Searle et al. | |
| 7,074,979 B2 | 7/2006 | Van Egmond et al. | |
| 2003/0088136 A1 | 5/2003 | Lumgair et al. | 585/640 |

FOREIGN PATENT DOCUMENTS

WO     WO 02/00579     1/2002

OTHER PUBLICATIONS

Yang et al., "Physical and Chemical Properties and Handling Aspect", Chapter 2, pp. 554, Northwestern University, Evanston, Illinois (1994).

* cited by examiner

TREATING OXYGENATE CONTAINING FEEDSTREAMS IN THE CONVERSION OF OXYGENATES TO OLEFINS

CROSS REFERENCE

This application is a continuation in part of U.S. Ser. No. 10/304,328 filed Nov. 26, 2002 now U.S. Pat. No. 6,846, 966, and U.S. Ser. No. 10/421,012 filed Apr. 22, 2003 now U.S. Pat. No. 7,074,979, which claims the benefit of U.S. Provisional No. 60/437,698 filed Dec. 31, 2002, the entire contents of these applications are herein incorporated by reference.

FIELD OF THE INVENTION

The invention relates to treating an oxygenate-containing feedstream. More particularly, this invention is directed to removing contaminants from an oxygenate-containing feedstream for an oxygenate to olefin reaction system.

BACKGROUND OF THE INVENTION

Light olefins, defined herein as ethylene, propylene, butylene and mixtures thereof, serve as feeds for the production of numerous important chemicals and polymers. Typically, light olefins are produced by cracking petroleum feeds. Because of the limited supply of competitive petroleum feeds, the opportunities to produce low cost light olefins from petroleum feeds are limited. Efforts to develop light olefin production technologies based on alternative feeds have increased.

An important type of alternate feed for the production of light olefins are oxygenates, such as, for example, alcohols, particularly methanol, ethanol, n-propanol, and iso-propanol, dimethyl ether, methyl ethyl ether, diethyl ether, dimethyl carbonate, and methyl formate. Many of these oxygenates may be produced by fermentation, or from synthesis gas derived from natural gas, petroleum liquids, carbonaceous materials, including coal, recycled plastics, municipal wastes, or any organic material. Because of the wide variety of sources, alcohol, alcohol derivatives, and other oxygenates have promise as an economical, non-petroleum source for light olefin production.

Oxygenates can be converted to olefins using various molecular sieve catalysts. This conversion of oxygenates to olefins (OTO) is an exothermic process. Therefore, the reactor outlet temperature is typically higher than the reactor inlet temperature.

Many methods and/or process schemes have been proposed to manage the heat of reaction generated from the exothermic process in order to avoid temperature surges and hot spots. A well managed process can also lead to a reduction of the rate of catalyst deactivation, as well as the production of undesirable products, such as methane, ethane, carbon monoxide and carbonaceous deposits or coke. Such processes tend to involve heating the feed or cooling the effluent to appropriate temperatures and pressures.

U.S. Pat. No. 6,121,504 (Kuechler et al.) discloses a process for catalytically converting a feedstock comprising an oxygenate to olefins. The process includes direct product quenching to increase heat recovery and to improve heat integration. In particular, a heavy product formed in the reaction process is used to provide at least a portion of the heat used to heat the feedstock.

U.S. Patent Application Publication, Pub. No. US 2003/0088136 A1, published May 8, 2003, discloses a process for recovering heat in an oxygenate to olefin production process. The process includes removing heat while maintaining the temperature of an effluent gas stream above the dew point temperature of the effluent gas stream. A step of washing the effluent gas stream to remove solid catalyst particles from the gas stream is also provided.

Well managed utilization of heat in the oxygenate to olefins conversion processes are continuously sought. In addition, well managed processes that result in the reduction of the rate of catalyst deactivation or a reduction in production of undesirable products are also continuously sought.

SUMMARY OF THE INVENTION

This invention provides well managed processes for converting oxygenates to olefins. The processes provide efficient utilization of heat, lead to a reduction in rate of catalyst deactivation, and aid in maintaining long term selectivity to desired olefin products, particularly ethylene and propylene.

In one aspect, this invention provides a process for removing metalloaluminophosphate molecular sieve contaminants from an oxygenate feed and converting the oxygenate in the feed to olefin product. In one, embodiment the processes comprises heating the oxygenate feed to form a vapor stream containing a majority of oxygenates in the oxygenate feed and a liquid stream containing a majority of metalloaluminophosphate molecular sieve contaminants in the oxygenate feed. The vapor stream is separated from the liquid stream; and the separated vapor stream is contacted with metalloaluminophosphate molecular sieve to convert the oxygenates in the stream to olefin product.

In another embodiment, there is provided a process for converting oxygenate feed to olefin product, which comprises heating an oxygenate feed comprising methanol and metalloaluminophosphate molecular sieve catalyst contaminants, at atmospheric pressure or above, to at least the boiling point of the methanol at the pressure at which the oxygenate feed is heated, to form a vapor stream containing a majority of the methanol in the oxygenate feed and a liquid stream containing a majority of metalloaluminophosphate molecular sieve contaminants in the oxygenate feed. The vapor stream is separated from the liquid stream, with the liquid stream comprising a majority of the metalloaluminophosphate molecular sieve catalyst contaminants in the oxygenate feed. The separated vapor stream is contacted with metalloaluminophosphate molecular sieve catalyst to convert the methanol in the vapor stream into olefin product.

The invention further provides a process for forming an olefin product, which comprises the steps of making methanol and converting the methanol to olefin product. In one embodiment, the process comprises contacting a synthesis gas with a carbon oxide conversion catalyst to form a feedstream that comprises methanol. The feedstream is transported in a container to a location geographically distinct from that where the feedstream was formed, and the transported feedstream is heated to form a vapor stream and a liquid stream. Preferably, the vapor stream comprises a majority of the methanol in the feedstream, and the liquid stream contains metalloaluminophosphate molecular sieve contaminants. The vapor stream is separated from the liquid stream, and the separated vapor stream is contacted with metalloaluminophosphate molecular sieve to convert the methanol in the feedstream to olefin product.

In one preferred embodiment, the vapor stream contacting the metalloaluminophosphate molecular sieve contains at least 75 wt % of the oxygenates in the oxygenate feed. Preferably, the vapor stream contacting the metalloaluminophosphate molecular sieve contains at least 85 wt %, more preferably at least 95 wt %, and most preferably at least 98 wt % of the oxygenates in the oxygenate feed. Preferably, the oxygenate feed comprises methanol. More preferably, a majority of the oxygenate in the oxygenate feed is methanol. It is particularly desirable that the vapor stream contain at least 75 wt %, more preferably at least 85 wt %, still more preferably at least 95 wt %, and most preferably at least 98 wt % of the methanol that is present in the oxygenate feed.

In another embodiment of the invention, at least a portion of the liquid stream is discarded and the discarded portion contains at least 75 wt % of the metalloaluminophosphate molecular sieve contaminants in the oxygenate feed. Preferably, the discarded portion contains at least 80 wt %, more preferably at least 85 wt %, and most preferably at least 90 wt % of the metalloaluminophosphate molecular sieve contaminants in the oxygenate feed. The metalloaluminophosphate molecular sieve contaminants can be non-volatiles or partial volatiles.

When the oxygenate feed contains methanol as a major oxygenate component, the oxygenate feed is heated to a temperature that is greater than or equal to the boiling point of methanol at the pressure at which the oxygenate feed is heated. Preferably, the oxygenate feed is heated to a temperature that is lower than the boiling point of 1-octene at the pressure at which the oxygenate feed is heated.

In yet another embodiment of the invention, the oxygenate feed is heated to form a vapor stream at a temperature that is not greater than 200° C. Preferably, the oxygenate feed is heated to form a vapor stream at a temperature that is not greater than 150° C.

In a preferred embodiment of the invention, at least a portion of the liquid stream is separated from the vapor stream is ultimately discarded. The discarded liquid stream will preferably contain a substantial quantity of metalloaluminophosphate molecular sieve contaminants. Preferably, the metalloaluminophosphate molecular sieve catalyst contaminants in the discarded portion include at least one metal selected from the group consisting of iron, sodium and potassium. In one embodiment, the discarded portion has a total iron, sodium and potassium concentration of at least 1 wppm, based on total weight of the liquid stream. Preferably, the discarded portion has a total iron, sodium and potassium concentration of at least 5 wppm, more preferably at least 10 wppm, based on total weight of the liquid stream.

In another embodiment of the invention, the vapor stream contacting the metalloaluminophosphate molecular sieve contains not greater than 5 wppm of any one metal selected from the group consisting of iron, sodium and potassium, based on total weight of the vapor stream contacting the sieve. Preferably, the vapor stream contacting the metalloaluminophosphate molecular sieve contains not greater than 2 wppm, more preferably not greater than 1 wppm, and most preferably not greater than 0.5 wppm of any one metal selected from the group consisting of iron, sodium and potassium, based on total weight of the vapor stream contacting the sieve.

The processes of the invention preferably include a step of discarding at least a portion of the separated liquid stream so that contaminants in the stream do not come into contact with the metalloaluminophosphate molecular sieve and adversely affect the activity or life of the sieve. The steps of heating the oxygenate and separating the vapor stream can be carried out in one or more stages.

The invention also provides a process for shipping methanol and converting the methanol to olefin product. According to such a process, the methanol is loaded into a hold of a ship, and the methanol is transported to a location geographically distinct from where the methanol was loaded into the ship. At least a portion of the methanol is withdrawn from the hold, and a blanketing medium, preferably a gas, is added to the hold. The withdrawn methanol is heated to form a vapor stream that comprises a majority of methanol and a liquid stream that contains metalloaluminophosphate molecular sieve contaminants. The vapor stream is separated from the liquid stream, and the separated vapor stream is contacted with metalloaluminophosphate molecular sieve to convert the methanol to olefin product.

BRIEF DESCRIPTION OF THE DRAWINGS

Examples of the various embodiments of this invention are shown in the attached Figures, wherein.

DETAILED DESCRIPTION OF THE INVENTION

Figure 1:
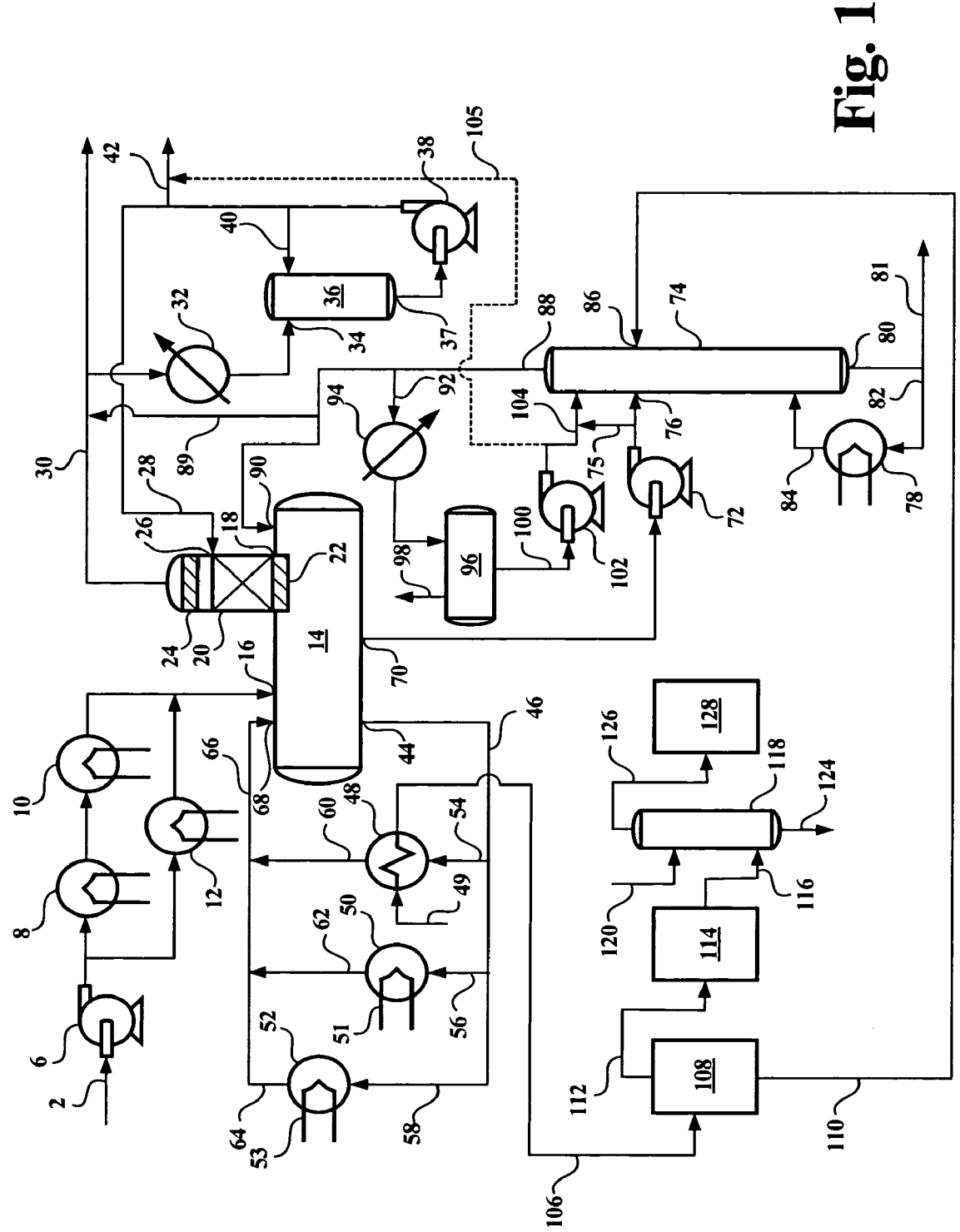
FIG. 1 is a flow diagram of one embodiment of the present invention.

I. Removal of Contaminants from Reaction Process

This invention provides for a significant reduction of contaminant materials in an oxygenate stream. Such a stream is particularly beneficial when used as a feedstream in the conversion of the oxygenates in the feedstream to olefin products, particularly ethylene and propylene products. Such contaminants include a variety of non-volatile, as well as partially volatile, compounds that act to reduce catalyst life or selectivity to the desired product, particularly ethylene and propylene content in the product.

The processes of the invention are particularly directed to reaction systems that incorporate the use of metalloaluminophosphate molecular sieves to convert the oxygenates in the feed to olefins. Of particular interest in the invention is the removal of contaminants from oxygenate streams comprising methanol as the major component.

It has now been found that even the more highly pure forms of oxygenates available at commercial scale quantities can contaminate metalloaluminophosphate molecular sieve catalyst, if the oxygenates are not properly controlled during a heat-up phase of the reaction process. For example, it has now been found that conventional heating of highly pure forms of methanol streams, such as grade A or AA methanol streams, leads to a loss of catalytic lifetime of metalloaluminophosphate molecular sieves. This loss of lifetime in turn reduces the long term selectivity to ethylene and propylene in the olefin product.

According to the processes of this invention, oxygenate feeds used in the conversion of oxygenates to olefins are heated in a heating system to form a vapor stream and a liquid stream. That is, at least a portion of the oxygenate feed is vaporized in the heating system. The heating system can be one or more stages. The more stages, the more effective the contaminant removal. Multiple stages can be carried out in one vessel or in more than one vessel. There can also be more than one vapor stream and more than one liquid stream formed in multi-stage embodiments. A primary focus of this invention, however, is the final product vapor stream and the final product liquid stream that is discarded from the system. The final product vapor stream is of high quality and will ultimately contact the metalloaluminophospohate molecular sieve. The discarded liquid stream will contain a substantial amount of contaminants originally present in the oxygenate feedstock. A least a portion of the liquid stream is discarded (i.e., not allowed to contact the metalloaluminophospohate molecular sieve), so as not to negatively impact the molecular sieve.

Once the vapor stream formed by the processes of this invention leaves the heating system, the vapor stream can be further heated or treated if desired. For example, the stream coming out of the system can be superheated if desired to further adjust the temperature of the stream prior to entering the reactor containing the metalloaluminophosphate molecular sieve.

The liquid stream leaving the system can also be further treated if desired. A liquid stream leaving the system is one that is not further heated or treated to recover additional oxygenate from the liquid stream, and to use that additional oxygenate as a feedstock for any other conversion process, such conversion process including the conversion of the oxygenate to olefin product or any other conversion process. For example, the liquid stream leaving the system can be sent directly to a wastewater treatment system or it can be sent to some other system such as a metals recovery system.

The heating of the oxygenate feed is conducted so that a majority of the metalloaluminophosphate molecular sieve catalyst contaminants in the feed is contained in the liquid stream. The vapor stream is separated from the liquid stream, and the separated vapor stream is contacted with the metalloaluminophosphate molecular sieve catalyst to form olefin product. The vapor stream is low in contaminants so that the metalloaluminophosphate molecular sieve catalyst is able to operate in the reaction system over an extended period of time with little to no contamination problems. Thus, the catalyst will be able to maintain its selectivity to ethylene and propylene over an extended period of time.

In one embodiment, all or a part of the liquid stream is discarded. If the oxygenate feedstream contains low levels of contaminants, only a relatively small liquid stream need be formed and/or discarded.

In another embodiment, the formation of a vapor stream and the separation of that stream from a liquid stream are carried out in a system having more than one stage. A heating system that employs more than one stage can include one or more vessels. Non limiting examples of vessels or equipment that can be used in multi-stage systems include one or more distillation columns, thermosiphon exchangers, vapor-liquid separation drums and kettle-type exchangers used alone or in any variety of combinations. Multi-stage systems that use more than one vessel for heating and separation of the vapor stream from the liquid stream can form additional liquid streams between stages. The final liquid stage leaving the system generally contains the highest level of contaminants and is desirably discarded so as not to contact the contaminants with the metalloaluminophosphate molecular sieve.

In one type of a multi-stage heating system, a liquid stream that is formed during a first heating step contains a portion of the oxygenate that was originally in the feedstream. If the oxygenate in the liquid stream is of significant quantity, then the oxygenate remaining in the liquid stream can be recovered in one or more subsequent or intermediate stages and used as feed. For example, a liquid stream comprising at least about 3 wt % or 5 wt % or 10 wt % of the major feed oxygenate component, particularly methanol, can be further processed, such as by additional heating, to recover a significant portion of the major feed component. Preferably, in this embodiment, at least a portion of the liquid stream formed during the first heating step is sent to a second or subsequent heating step to form one or more additional vapor streams, with the additional vapor stream comprising at least a majority of the oxygenate contained in the liquid stream formed during the first heating step. The second or subsequent vapor stream can then be used as additional feed in the conversion reaction. The remaining liquid stream contains a substantial quantity of the metalloaluminophosphate molecular sieve catalyst contaminants. Preferably, all or a portion of the remaining stream is discarded.

Components that are considered metalloaluminophosphate molecular sieve catalyst contaminants in this invention are those components in the oxygenate feedstream that significantly reduce metalloaluminophosphate molecular sieve catalyst lifetime or selectivity to ethylene and propylene. Such contaminants include non-volatile materials or non-volatiles and partial non-volatiles as further defined herein. Contaminants that have an especially negative impact on the metalloaluminophosphate molecular sieve catalyst are catalyst lifetime reducing or catalyst selectivity reducing metals. Examples of such metals include iron, sodium and potassium. Such metals can be found in the oxygenate feedstream as a result of using low grade feed or as a result of having relatively pure grades of feed being contaminated during transport or storage.

In one embodiment of the invention, an oxygenate feedstream is transported in a container to a location geographically distinct from where the feedstream was produced. The transported oxygenate is then treated according to a process of this invention to heat the feed and remove contaminants, such as metals, added to the feed during transport.

In another embodiment, an oxygenate feedstream is transported through a pipeline system to an oxygenate conversion system. The pipeline system can include various pipes, valves, pumps, tanks, and process equipment that can add contaminants to the oxygenate. The transported oxygenate is treated according to a process of this invention to heat the oxygenate and remove the contaminants, such as metals, added during transport.

In one embodiment, the oxygenate feedstream, preferably a methanol containing feedstream, is manufactured at a site remote from where it is to be used as feed for a reaction system, and transported to the site of the reaction system where the feedstream is to be used. Preferably, the oxygenate feedstream is loaded into a vessel, and the vessel is transported over a body of water to a storage facility. The oxygenate can be easily transported at least 100, 500 or 1,000 miles or more. Once arriving at the storage facility, the oxygenate feedstream is delivered to a storage tank. From the storage tank, the oxygenate feedstream is ultimately sent to an olefin conversion unit for conversion to an olefin product. The oxygenate feedstream is preferably, loaded onto a ship, with the ship able to contain at least 20,000 tons, preferably at least 40,000 tons, and more preferably at least 80,000 tons. The ship is preferably a ship that has been modified according to various aspects of this invention, further described below.

In one embodiment of the invention, the oxygenate feed is heated to form a vapor stream and a liquid stream. The vapor stream contains a majority of the oxygenates that were in the oxygenate feed, and the liquid stream contains a majority of the metalloaluminophosphate molecular sieve contaminants that were in the oxygenate feed.

In a particular embodiment, the vapor stream that is separated from the oxygenate feedstream and contacts the metalloaluminophosphate molecular sieve contains at least 75% of the oxygenates in the original oxygenate feedstream, based on total weight of oxygenates in the original oxygenate feedstream. Preferably, the vapor stream contacting the molecular sieve contains at least 85%, more preferably at least 95%, and most preferably at least 98% of the oxygenates in the original oxygenate feedstream, based on total weight of oxygenates in the original oxygenate feedstream. Preferably, the oxygenate feedstream is a methanol feedstream.

In another embodiment, the liquid stream that is recovered from the heating process, preferably as the final liquid stream recovered from the heating process, contains at least 75% of the metalloaluminophosphate molecular sieve contaminants present in the original oxygenate feedstream, based on total weight of metalloaluminophosphate molecular sieve contaminants in the original oxygenate feedstream. Preferably, the recovered liquid stream contains at least 80%, more preferably at least 85%, even more preferably at least 90%, and most preferably at least 95% of the metalloaluminophosphate molecular sieve contaminants originally present in the oxygenate feedstream, based on total weight of metalloaluminophosphate molecular sieve contaminants in the original oxygenate feedstream. In a preferred embodiment, this recovered liquid stream is discarded as a waste stream to avoid contact of the contaminants in the stream with the metalloaluminophosphate molecular sieve.

The oxygenate feed is heated so as to vaporize a majority of the primary oxygenate feed component in the oxygenate feedstream, while keeping a majority of the metalloaluminophosphate molecular sieve contaminants in the liquid stream that exits the overall contaminant removal process. For example, when the primary oxygenate feed component is methanol, the oxygenate feed is heated to a temperature that is greater than or equal to the boiling point of methanol at the pressure at which the oxygenate feed is heated. In this case, the vapor will contain methanol, components that have a boiling point less than that of methanol, and some components that have a boiling point greater than that of methanol.

In one embodiment, the oxygenate feedstream is comprised of a majority of methanol (i.e., greater than 50 wt % methanol), and the oxygenate feedstream is heated so as to vaporize at least a portion of the methanol in the feedstream. Preferably, the oxygenate feedstream is heated so as to vaporize at least a majority of the methanol, preferably at least about 75 wt %, more preferably at least about 85 wt %, and most preferably at least about 95 wt %, based on total weight of methanol in the feedstream.

In another embodiment, the oxygenate feedstream is heated so that predominantly $C_8$ olefins and heavier compounds remain in the liquid state, while a substantial portion of the remaining feedstream is vaporized. Preferably, the feedstream is comprised of a majority of methanol (i.e., greater than 50 wt % methanol), and the oxygenate feedstream is heated so as to vaporize at least a portion of the methanol in the feedstream and a majority of $C_8$ olefins and heavier compounds in the feedstream remain in the liquid state. More specifically, the oxygenate feed is heated to a temperature that is lower than the boiling point of 1-octene at the pressure at which the oxygenate feed is heated.

The pressure at which the oxygenate feed is heated can vary, but it is preferred to heat at a pressure that is not considered high pressure. For example, the oxygenate feed can be heated in a vaporization system at a pressure ranging from about atmospheric pressure to about 350 psia (2413 kPa), preferably from about atmospheric pressure to about 200 psia (1379 kPa), and more preferably from about atmospheric pressure to about 100 psia (690 kPa). The vaporization system can include one or more heating stages.

The temperature at which the oxygenate feed is heated within the heating system of this invention varies according to the pressure at which the system is operated, and according to the components in the feedstream that are desired to be vaporized. The temperature of the heating or vaporization system can be carried out in one or more stages, with each stage being at a temperature that is at least at the boiling point temperature of the predominant oxygenate in the feed (e.g., at least at the boiling point of methanol when the predominant oxygenate in the feedstock is methanol). Clearly, the higher the pressure, the higher the temperature needed to vaporize the liquid components of the feedstream. In a preferred embodiment, the oxygenate feed is heated within the system to form a vapor stream at a temperature that is not greater than 200° C. Preferably, the oxygenate feed is heated to form a vapor stream at a temperature that is not greater than 150° C., and more preferably not greater than 125° C. If desired, the vapor stream can be further heated outside the system prior to contacting the metalloaluminophosphate molecular sieve. For example, the vapor stream can be superheated outside the system, such as to a temperature of greater than 200° C. or greater than 250° C., depending upon desired operating temperature of the desired oxygenate conversion reaction.

In one embodiment of the invention, control of the amount of metalloaluminophosphate molecular sieve catalyst contaminants that are carried with the vapor stream is based on the amount of the metalloaluminophosphate molecular sieve catalyst contaminants in the liquid stream. In one aspect, the metalloaluminophosphate molecular sieve catalyst contaminants include at least one metal selected from the group consisting of iron, sodium and potassium, and the liquid stream contains a majority of one or more of those metals from the oxygenate feedstream. Preferably, the oxygenate stream is vaporized to form a vapor stream and a liquid stream in one or more stages. Desirably, and the liquid stream from the final stage of the heating or vaporization process has a total iron, sodium and potassium concentration of at least 1 wppm, based on total weight of the final stage liquid stream. Preferably, the liquid stream from the final stage of the heating or vaporization process has a total iron, sodium and potassium concentration of at least 5 wppm, more preferably at least 10 wppm, and most preferably at least 50 wppm, based on total weight of the liquid stream.

The vaporization of the oxygenate feedstream and the removal of the resulting vapor stream is controlled so that only very low amounts of contaminants are carried over to the vapor stream that ultimately contacts the metalloaluminophosphate molecular sieve. Desirably, the separated vapor stream that contacts the molecular sieve contains not greater than 5 wppm of any one metal selected from the group consisting of iron, sodium and potassium, based on total weight of the vapor stream. The vapor stream can be a combination of one or more vapor streams that are incorporated in the overall process. For example, in multi-stage heating or vaporization stages, there will be more than one vapor stream formed and separated from as many liquid streams. Preferably, these separated vapor streams are combined and used as feed to contact the metalloaluminophosphate molecular sieve. It is preferred that the vapor stream that ultimately contacts the metalloaluminophosphate molecular sieve contains not greater than 2 wppm, more preferably not greater than 1 wppm, and most preferably not greater than 0.5 wppm of any one metal selected from the group consisting of iron, sodium and potassium, based on total weight of the separated vapor stream.

Various methods of determining the metals content of the various streams can be used in this invention. One preferred method, however, is the current standard version of ASTM D-5863.

The liquid stream that is ultimately recovered from the heating or vaporization system preferably contains relatively low concentrations of oxygenates and relatively high concentrations of contaminants. In cases where the liquid stream contains a relatively small volume of the major oxygenate component of the oxygenate feedstream, the entire liquid stream can be discarded. In cases where the liquid stream comprises a significant amount of the major oxygenate component of the oxygenate feedstream, the liquid stream is recovered, and at least a portion of the oxygenate is separated from the recovered liquid stream. This is preferably accomplished though additional heating stages by additional vaporization of the oxygenate. This oxygenate can be used as a feedstream for the oxygenate to olefin reaction system. In either event, at least a portion of the liquid stream is discarded to remove the contaminants from the system to minimize damage to the metalloaluminophosphate molecular sieve catalyst.

II. Types of Oxygenate Feed

A. Oxygenates in General

Oxygenates that can be used as the feedstream of this invention preferably comprise one or more aliphatic-containing compounds that include alcohols, amines, carbonyl compounds for example aldehydes, ketones and carboxylic acids, ethers, halides, mercaptans, sulfides, and the like, and mixtures thereof. The aliphatic moiety of the aliphatic-containing compounds typically contains from about 1 to about 50 carbon atoms, preferably from about about 1 to about 20 carbon atoms, more preferably from about 1 to about 10 carbon atoms, and most preferably from about 1 to about 4 carbon atoms.

Non-limiting examples of aliphatic-containing compounds include alcohols such as methanol and ethanol, alkyl-mercaptans such as methyl mercaptan and ethyl mercaptan, alkyl-sulfides such as methyl sulfide, alkyl-amines such as methyl amine, alkyl-ethers such as dimethyl ether, diethyl ether and methylethyl ether, alkyl-halides such as methyl chloride and ethyl chloride, alkyl ketones such as dimethyl ketone, formaldehydes, and various acids such as acetic acid.

In a preferred embodiment of the process of the invention, the feedstock contains one or more oxygenates, more specifically, one or more organic compounds containing at least one oxygen atom. In the most preferred embodiment of the process of the invention, the oxygenate in the feedstock is one or more alcohols, preferably aliphatic alcohols where the aliphatic moiety of the alcohols has from about 1 to about 20 carbon atoms, preferably from about 1 to about 10 carbon atoms, and most preferably from about 1 to about 4 carbon atoms. The alcohols useful as feedstocks in the process of the invention include lower straight and branched chain aliphatic alcohols and their unsaturated counterparts. Non-limiting examples of oxygenates include methanol, ethanol, n-propanol, isopropanol, methyl ethyl ether, dimethyl ether, diethyl ether, di-isopropyl ether, formaldehyde, dimethyl carbonate, dimethyl ketone, acetic acid, and mixtures thereof. In the most preferred embodiment, the feedstock is selected from one or more of methanol, ethanol, dimethyl ether, diethyl ether or a combination thereof, more preferably methanol and dimethyl ether, and most preferably methanol.

B. Methanol Containing Feedstream

In one embodiment of this invention, the feedstream is a methanol feedstream. The methanol feedstream can be of a highly pure form, such as commercial grade A or AA methanol, or it can contain various contaminants such as can be found in crude grade methanol. Examples and uses of such grades of methanol are found in U.S. Pat. No. 6,444,712 B1 (Janda); U.S. Pat. No. 6,486,219 B1 (Janda); U.S. Pat. No. 4,592,806 (Ilgner); and U.S. Pat. No. 5,714,662 (Vora), the contents of each being fully incorporated herein by reference. An advantage of this invention is that the heat and contaminant removal steps of the invention allow for the use of a wide variety of grades of methanol as feedstock for the oxygenate to olefins conversion reaction systems.

When used in this invention, the methanol feedstock can be manufactured from a variety of carbon sources or hydrocarbon feedstreams. Examples of such sources include biomass, natural gas, $C_1$–$C_5$ hydrocarbons, naphtha, heavy petroleum oils, or coke (i.e., coal). Preferably, the carbon source is a hydrocarbon feedstream that comprises methane in an amount of at least about 50% by volume, more preferably at least about 70% by volume, most preferably at least about 80% by volume. In one embodiment of this invention natural, gas is the hydrocarbon feedsource.

One way of converting the carbon source to a methanol composition is to first convert the carbon source to synthesis gas (syngas), and then convert the syngas to the methanol composition. Any conventional process can be used. In particular, any conventional carbon oxide conversion catalyst can be used to convert the syngas to the methanol composition. In one embodiment, the carbon oxide conversion catalyst is a nickel containing catalyst.

Synthesis gas comprises carbon monoxide and hydrogen. Optionally, carbon dioxide and nitrogen are included. Conventional processes for converting carbon components to syngas include steam reforming, partial oxidation, and autothermal reforming.

The synthesis gas is sent to a methanol synthesis process and converted to a methanol composition. The methanol synthesis gas process is accomplished in the presence of a methanol synthesis catalyst.

In one embodiment, the synthesis gas is sent directly to the methanol synthesis process without adjustment. In another embodiment, the hydrogen, carbon monoxide, and/or carbon dioxide content of the synthesis gas is adjusted for efficiency of conversion. Desirably, the synthesis gas input to the methanol synthesis reactor has a molar ratio of hydrogen ($H_2$) to carbon oxides ($CO+CO_2$) in the range of from about 0.5:1 to about 20:1, preferably in the range of from about 2:1 to about 10:1. In another embodiment, the synthesis gas has a molar ratio of hydrogen ($H_2$) to carbon monoxide (CO) of at least 2:1. Carbon dioxide is optionally present in an amount of not greater than 50% by weight, based on total weight of the synthesis gas.

Desirably, the stoichiometric molar ratio is sufficiently high so as maintain a high yield of methanol, but not so high as to reduce the volume productivity of methanol. Preferably, the synthesis gas fed to the methanol synthesis has a stoichiometric molar ratio (i.e., a molar ratio of $H_2$:($2CO+3CO_2$)) of from about 1.0:1 to about 2.7:1, more preferably from about 1.1 to about 2.0, more preferably a stoichiometric molar ratio of from about 1.2:1 to about 1.8:1.

The $CO_2$ content, relative to that of CO, in the synthesis gas should be high enough so as to maintain an appropriately high reaction temperature and to minimize the amount of undesirable by-products such as paraffins. At the same time, the relative $CO_2$ to CO content should not be too high so as to reduce methanol yield. Desirably, the synthesis gas contains $CO_2$ and CO at a ratio of from about 0.5 to about 1.2, preferably from about 0.6 to about 1.0.

In one embodiment, the catalyst used in the methanol synthesis process includes an oxide of at least one element selected from the group consisting of copper, silver, zinc, boron, magnesium, aluminum, vanadium, chromium, manganese, gallium, palladium, osmium and zirconium. Preferably, the catalyst is a copper-based catalyst, more preferably in the form of copper oxide.

In another embodiment, the catalyst used in the methanol synthesis process is a copper based catalyst, which includes an oxide of at least one element selected from the group consisting of silver, zinc, boron, magnesium, aluminum, vanadium, chromium, manganese, gallium, palladium, osmium and zirconium. Preferably, the catalyst contains copper oxide and an oxide of at least one element selected from the group consisting of zinc, magnesium, aluminum, chromium, and zirconium. More preferably, the catalyst contains oxides of copper and zinc.

In yet another embodiment, the methanol synthesis catalyst comprises copper oxide, zinc oxide, and at least one other oxide. Preferably, the at least one other oxide is selected from the group consisting of zirconium oxide, chromium oxide, vanadium oxide, magnesium oxide, aluminum oxide, titanium oxide, hafnium oxide, molybdenum oxide, tungsten oxide, and manganese oxide.

The methanol synthesis process is effective over a wide range of temperatures. In one embodiment, the synthesis gas is contacted with the methanol synthesis catalyst at a temperature in the range of from about 150° C. to about 450° C., preferably in a range of from about 175° C. to about 350° C., more preferably in a range of from about 200° C. to about 300° C.

The process is also operable over a wide range of pressures. In one embodiment, the synthesis gas is contacted with the methanol synthesis catalyst at a pressure in the range of from about 15 atmospheres to about 125 atmospheres, preferably in a range of from about 20 atmospheres to about 100 atmospheres, more preferably in a range of from about 25 atmospheres to about 75 atmospheres.

Gas hourly space velocities vary depending upon the type of continuous process that is used. Desirably, gas hourly space velocity of flow of gas through the catalyst bed is in the range of from about 50 $hr^{-1}$ to about 50,000 $hr^{-1}$. Preferably, gas hourly space velocity of flow of gas through the catalyst bed is in the range of from about 250 $hr^{-1}$ to about 25,000 $hr^{-1}$, more preferably from about 500 $hr^{-1}$ to about 10,000 $hr^{-1}$.

The methanol synthesis process produces a variety of hydrocarbons as by-products. In addition, there can be some carry over of any one or more of the metals used in the synthesis process into the methanol product composition. By-product formation or metals carry over can negatively impact metalloaluminophosphate molecular sieve catalyst used in converting the methanol product into olefin product. In addition, other contaminants can be picked up in the methanol product as it is transported to market. Such contaminants include non-volatile or low-volatile contaminants as described herein. In one embodiment, the contaminants include various metals such as iron, sodium and potassium, which can also negatively impact metalloaluminophosphate molecular sieve catalyst. Thus, the processes of this invention optionally call for the removal of such contaminants prior to contacting oxygenates such as methanol with the metalloaluminophosphate molecular sieve catalyst.

III. Shipping Oxygenate Feedstock

This invention is also directed to the transport of oxygenate feedstock, with specific examples of transport of methanol feedstock. Although many of the examples provided herein are directed to the transport of methanol, it is to be understood that the problems associated with transport of methanol generally apply to the transport of oxygenates that are conventionally used in the conversion of oxygenates to olefins.

This invention is particularly well suited for selectively removing non-volatile and low-volatile (e.g., partially volatile) contaminants from an oxygenate-containing feed that has been transported by tankers. Low levels of various volatile contaminants such as $SO_x$, carbonic acid, and $C_5$– hydrocarbons, however, do not significantly affect catalytic activity or the oxygenate conversion process, and may be allowed to enter the oxygenate conversion reactor.

In one embodiment of this invention, a methanol feedstock that is not of high quality, such a grade not meeting Grade A or AA methanol specifications, is used in the oxygenate conversion process. In particular, contaminants in methanol resulting from uncoated tanker holds and/or from a blanketing medium will not significantly impact the oxygenate conversion process. Therefore, when using ships with tank holds greater than 3,000 $m^3$ in volume, a non-nitrogen blanketing system is sufficient to satisfy the SOLAS resolution and deliver an acceptable oxygenate conversion feedstock. Crude and naphtha-carrying tankers are plentiful and generally much less expensive to build or modify than conventional large methanol-carrying tankers because they typically do not have coated holds or expensive inerting systems.

As used herein, "naphtha" means a refined petroleum material containing $C_5$+ hydrocarbons. A non-limiting list of exemplary naphthas includes refined gasoline, raw gasoline, natural gasoline, and field condensates. The costs associated with shipping methanol destined for an oxygenate conversion reactor system may be greatly reduced from conventional methanol shipping costs by modifying a conventional crude or naphtha-carrying tanker to carry various grades of methanol.

In one embodiment, a relatively inexpensive process is provided for modifying conventional crude/naphtha-carrying tankers to ship methanol. The process includes one or more of the following steps: (1) cleaning the holds of the crude/naphtha-carrying tanker to remove residual deposits, wherein the holds previously stored a non-methanol material; (2) providing a fire suppression system specially designed to prevent methanol fires; and (3) replacing methanol intolerant pump seals and flange gaskets in the tanker with methanol resistant seals and gaskets. The fire suppression system includes a fire suppression conduit system for delivering the alcohol resistant fire suppression agent to the tanker holds.

A methanol blanketing system is also provided, which includes a blanketing medium generator in a tanker for generating a blanketing medium selected from the group consisting of: exhaust gases from a diesel engine, a gas oil engine, a kerosene engine, a gasoline engine and a methanol engine. Additionally or alternatively, the blanketing medium generator is a diesel, gas oil, kerosene, methanol or gasoline burner having a combustion chamber, or any other fuel burning engine or burner. Both the engine and the burner style blanketing medium generators provide a satisfactory blanketing medium, which optionally includes water-saturated carbon dioxide. A conduit system is also provided, which is in communication with the blanketing medium generator and one or more holds. The blanketing medium generator directs the blanketing medium through the conduit system to the one or more holds, the holds being at least partially filled with a fluid cargo comprising methanol.

Additionally, a process is provided for unloading methanol from a tanker. The process includes withdrawing at least a portion of the methanol from a hold, and replacing the volume of the withdrawn methanol with a blanketing medium. The blanketing medium is selected from the group consisting of: exhaust from a diesel, gas oil, kerosene, methanol, or gasoline engine. Additionally or alternatively, the blanketing medium is provided by a diesel, gas oil, kerosene, methanol or gasoline burner. The blanketing medium may include carbon dioxide, carbon monoxide, soot, $SO_x$, particulate contaminants or a combination thereof.

In one embodiment, the present invention is directed to a process for modifying a tanker for carrying methanol destined for use as a feedstock in an oxygenate conversion reaction system. The process includes: (1) cleaning the holds of the crude/naphtha-carrying tanker to remove residual deposits; (2) providing a fire suppression system for delivering an alcohol-resistant fire suppression agent; and (3) replacing methanol intolerant seals and/or gaskets in the tanker with methanol resistant seals and/or gaskets. The process optionally includes providing a blanketing system, which delivers a blanketing medium to the holds. In another embodiment, the invention is directed to a process for converting methanol to light olefins wherein the methanol does not pass specification for Grade A or AA methanol. In other embodiments, the invention is directed to a tanker modified by the above process, a methanol blanketing system, a process for unloading methanol from a tanker, and a process for providing methanol to an oxygenate conversion reaction system.

The conversion of oxygenate to olefins involves contacting methanol with a molecular sieve catalyst under conditions effective to convert at least a portion of the methanol to light olefins, e.g., ethylene and propylene. It has been discovered that a methanol-containing stream containing a certain level of contaminants may be, depending on the type and amount of contaminant, provided directly to an oxygenate conversion reaction system without significantly affecting the oxygenate conversion reaction process. More specifically, it has been discovered that the catalysts implemented in the oxygenate conversion reaction process will not be significantly deactivated by select volatile contaminants such as $SO_x$, carbonic acid, and $C_5$-hydrocarbons. Vaporization of the methanol-containing feedstock prior to its introduction into an oxygenate conversion reactor also limits particulate and salt contamination or contamination by other non-volatile components, as described above. Thus, one embodiment of the invention is directed to a process for converting methanol that does not meet grade A or AA specifications to light olefins. Table 1 provides the requirements for Grades A and AA methanol.

TABLE 1

| Test | Grade A | Grade AA |
|---|---|---|
| IMPCA 001 Methanol | 99.85 wt. % Min. | 99.85 wt. % Min. |
| ASTM D346 Water | 1500 ppm wt. Max. | 1000 ppm wt. Max. |
| ASTM D1209 Color | 5 mg pt/liter Max. | 5 mg pt/liter Max. |
| ASTM D1078 Distillation | 149° F. ± 0.9 | 149° F. ± 0.9 |
| ASTM D1363 $KMnO_4$ test at 68° F. | 30 minutes | 30 minutes |
| ASTM D1722 Hydrocarbons | Pass test | Pass test |
| Visual Appearance | Clear & Colorless | Clear & Colorless |
| ASTM D891 Specific Gravity @ 68° F. | 0.791–0.792 | 0.791–0.792 |
| ASTM D1613 Acid Number | <0.03 mg KOH/g | <0.03 mg KOH/g |
| ASTM E346 Carbonyl number | <0.02 mg KOH/g | <0.02 mg KOH/g |
| ASTM D3961 Sulfur | 0.5 ppmw | 0.5 ppmw |

According to one aspect of this invention, a non-conventional methanol tanker, which might cause contamination of the methanol stored therein, may be used to transport methanol destined for an oxygenate conversion reaction system, particularly if the tanker is modified according to the invention. Although the methanol unloaded from these modified tankers may contain one or more volatile, non-volatile and/or low-volatile contaminants, the methanol may still be suitable for an oxygenate conversion reaction system. The tanker may or may not have previously carried a non-methanol material, such as naphtha or crude oil.

One embodiment of the invention is to a process for modifying a tanker to carry methanol. The process includes providing a tanker having one or more holds that previously stored and/or was designed to hold a non-methanol material. A fire suppression system is provided for delivering an alcohol resistant fire suppression agent to the holds. The fire suppression system preferably includes a conduit system for delivering the alcohol resistant fire suppression agent to the holds. The time required to accomplish the conversion on an existing standard Aframax product carrier is 2 to 5 months depending on the design of the ship.

Conventional fire suppression systems for tankers that are designed to carry a non-methanol cargo, e.g., naphtha or crude oil, typically include a fire suppression system storage tank, a pump and conduit lines, e.g., pipes, which transfer the fire suppression agent to outlet nozzles, e.g., turrets, which optionally are used to direct the suppression agent at a fire in one or more of the holds. Typically, the fire suppression agent for a non-methanol carrying tanker is a protein based or AFFF foam extinguishing material, which may be ineffective or unsatisfactory against a methanol fire. Specifically, alcohols may break down these conventional fire suppression agents causing them to reduce their extinguishing characteristics. The IBC code dictates the requirements for methanol fire suppression including the type and amount of foam required. Thus, in one embodiment of the invention, the fire suppression system is supplemented, replaced or modified to allow the suppression system to adequately deliver an alcohol-resistant fire suppression agent to the tanker holds.

A preferred alcohol-resistant fire suppression agent is a foam material, such as UNITOL fire suppression foam marketed by Unitor ASA (Oslo, Norway). The UNITOL fire suppression foam or other fire suppression foam to be implemented according to the present invention ideally has an increased surface tension so the foam preferably will not break apart when it contacts methanol. Specifically, the foam fire suppression agent preferably includes a surfactant, which prevents the foam from breaking up upon its release onto a methanol fire. Because foam materials are less dense than conventional fire suppression agents used in non-methanol carrying tankers, the tanker's fire suppression system should be modified in order to be able to adequately deliver the foam fire suppression agent to the tanker holds. Approximately twice as much alcohol resistant fire suppression agent than conventional fire suppression agent may be required. Accordingly, in accordance with the present invention, a fire suppression agent storage tank having increased volume should be provided that is capable of storing an alcohol-resistant fire suppression agent. The existing tank may be enlarged through well-known techniques, or supplemented with an additional fire suppression agent storage tank. Alternatively, the existing tank is removed and replaced with a larger storage tank better suited for storing an alcohol-resistant fire suppression agent.

Similarly, the conduit lines for transferring the fire suppression agent to the one or more outlets should be modified, supplemented with a second conduit system or replaced with a second conduit system to provide a final conduit system capable of delivering the alcohol-resistant fire suppression agent to the outlets and, ultimately, to the holds or tanker deck at a satisfactory flow rate to enable the extinguishing of a methanol fire. Preferably, the overall cross sectional area of the final conduit system will be larger than the preexisting conduit system in order to allow an increased flow capacity necessary for delivering a foam fire suppression agent to the outlets. Additionally or alternatively, the existing fire suppression conduit lines may be supplemented with an additional set of conduit lines to enable satisfactory delivery of the methanol-resistant fire suppression agent to the outlets.

The tanker also will likely have a preexisting pump adapted to deliver a liquid fire suppression agent to the conduit system. Pumping an alcohol-resistant fire suppression agent with the preexisting pump may not provide sufficient flow characteristics for the alcohol-resistant fire suppression agent. Accordingly, in one embodiment of the invention, the preexisting pump is replaced with a second pump adapted to pump the alcohol-resistant fire suppression agent at a sufficient volumetric flow rate. The second pump is adapted to pump the alcohol-resistant fire suppression agent from the storage tank to the conduit system and, ultimately, to the outlets and holds. In another embodiment, the preexisting pump is supplemented by a second pump, and the two or more pumps will operate simultaneously or intermittently in order to provide desirable pumping characteristics for the alcohol-resistant fire suppression agent. In another embodiment, the preexisting pump is modified, e.g., by increasing the size of the impeller, in order to provide desirable pumping characteristics for the alcohol-resistant fire suppression agent.

The fire suppression system optionally includes one, two, three, four or more fire suppression agent outlets. Each outlet preferably is an aimable turret adapted to direct and deliver the alcohol-resistant fire suppression agent toward the one or more holds or the tanker deck in order to extinguish any methanol fire present. Each turret preferably may be controlled by an individual who is able to aim the turret at a fire in one or more of the holds or on the deck of the tanker. Alternatively, a remote operating system is provided to operate the turret. In one embodiment, the preexisting nozzles are adapted to deliver the alcohol-resistant fire suppression agent. For example, the preexisting nozzles may be removed, replaced or modified with nozzles capable of delivering the alcohol-resistant fire suppression agent to the holds or the tanker deck. Each turret should be modified to include a nozzle creating a sufficient flow rate for the alcohol-resistant fire suppression agent. The fire suppression system also optionally includes one, two, three, four or more fire suppression agent turrets with modified nozzles.

In addition to providing a fire suppression system capable of delivering an alcohol-resistant fire suppression agent, the process for modifying a tanker to carry methanol preferably includes providing a gas blanketing system or an inerting system. A gas blanketing system is a system for delivering a gas blanketing medium to one or more of the tanker holds. The gas blanketing medium optionally comprises exhaust from a gasoline, kerosene, gas oil, methanol or diesel burning engine. Additionally or alternatively, the blanketing medium is provided by a diesel, gas oil, kerosene, gas oil, methanol or gasoline burner. A blanketing medium from a burner is referred to as flue gas. For tankers carrying methanol, a gas blanketing system is particularly desirable in order to reduce the amount of oxygen that contacts the methanol thereby decreasing the risk of a methanol fire. During the unloading of the methanol cargo, the blanketing medium is fed into the hold to replace the volume of methanol that is removed from the tanker hold.

An inerting system is a type of gas blanketing system wherein an inert gas, referred to generally as an inerting medium, such as nitrogen, acts as the blanketing medium. For example, in an inerting system, a nitrogen generator may be provided to supply nitrogen to the one or more holds. Nitrogen inerting systems, although more expensive than other blanketing systems, are well-known to be desirable for large methanol tankers because the inert gas does not impart contaminants to the methanol. Ships having tank holds smaller than 3,000 m$^3$ are not required by the SOLAS resolution to blanket methanol with a blanketing medium, and hence do not incur the cost of providing a blanketing system.

As it has been discovered that a non-grade A or AA methanol stream may be effectively directed to an oxygenate conversion reaction system, a tanker that previously carried or was designed to carry a non-methanol cargo may be modified to carry methanol destined for an oxygenate conversion reaction system by providing a gas blanketing system including a gasoline, kerosene, gas oil, diesel or methanol burning engine or a diesel, gas oil, kerosene, methanol or gasoline burner. The blanketing medium from the engine or burner is directed to the one or more methanol-containing holds. Although the blanketing medium from an engine or burner, depending on the fuel, will contain components such as $CO$, $CO_2$, and $SO_x$ and soot that will contaminate the methanol stored in the holds, the contaminated methanol may still be suitable for serving as a feedstock for an oxygenate conversion reaction system. Specifically, soot and other particulates are caught in an on-site tank system or in the liquid stream formed in the vaporization process, discussed above. Unburned $C_5$-hydrocarbons and sulfur are in small enough quantities as not to be considered an issue. Secondary contaminants, which are formed from one or more of these contaminants, also may contaminate the methanol stored in the holds, although the methanol may still be suitable for use in an oxygenate conversion reaction system. For example, $CO_2$ in methanol may form a secondary contaminant such as carbonic acid, which vaporizes with the oxygenate feed in the vaporization process. However, the presence of carbonic acid with the vaporized oxygenate feed does not render the methanol cargo unsuitable for use in an oxygenate conversion reaction system. Unlike conventional methanol-implementing processes such as MTBE and formaldehyde syntheses, the methanol feed preheat and vaporization process steps, discussed in detail above, will vaporize methanol away from soot particles and other non-volatiles contained in the feedstock. Limited amounts of volatiles such as $SO_x$, CO, carbonic acid and $C_5$-hydrocarbons may vaporize with the methanol and be transported to the reactor without significant detrimental effects on conversion or catalyst activity. Accordingly, if an unmodified tanker includes a gas blanketing system wherein the blanketing medium was exhaust or flue gas from a gasoline, kerosene, gas oil, or diesel engine or burner, the invention comprises placing methanol in the one or more holds and blanketing the methanol with the exhaust or flue gas from the gasoline, kerosene, gas oil or diesel engine or burner. The invention also includes selectively removing non-volatile contaminants, e.g., soot and rust, from the oxygenate feed, as discussed above. Unlike conventional large methanol-carrying tankers, the methanol is stored for transportation under a blanketing medium wherein the blanketing medium is exhaust from an engine or flue gas from a burner rather than nitrogen from a nitrogen generator. The blanketing medium generator optionally is upgraded by installing scrubbers to reduce the amount of soot, moisture, particulates and $SO_x$ in the gas to be used as the blanketing medium.

In another embodiment, the tanker is provided with an inerting system wherein the blanketing medium is an inert gas such as nitrogen. In this embodiment, the inerting system comprises an inerting medium generation unit, e.g., a nitrogen generator, which provides the inerting medium. The inerting system optionally is connected to a preexisting gas piping system thereby reducing installation costs.

Optionally, the tanker is provided with a methanol engine or burner, which forms exhaust or flue gas that serves as the blanketing medium. A blanketing medium from a methanol engine or burner is particularly clean and will not significantly contaminate the methanol cargo. In this embodiment, a small portion of the methanol cargo may be provided as fuel for the methanol engine or burner. One or more pumps, control devices and conduit lines may be provided to transport methanol from the one or more holds to the methanol engine or burner fuel tank or directly to the methanol engine or burner.

Regardless of the type of blanketing medium (engine exhaust, flue gas, inert gas or other blanketing medium), the blanketing system preferably includes one or more conduit lines, pumps and control devices for directing the blanketing medium to the one or more holds. If the tanker includes a plurality of laterally oriented holds, the blanketing system preferably includes at least two longitudinally extending conduit lines, which direct the blanketing medium to the holds. Each conduit line includes at least one outlet for each respective hold. The blanketing medium is directed through the lines and exits the conduit lines via the outlets. Optionally, the conduit line or lines include a plurality of outlets, e.g., 2, 3, 4 or more, for each respective hold.

Thus, one embodiment of the invention is a methanol blanketing system including a blanketing medium generator, e.g., a diesel, gasoline, methanol, gas oil, or kerosene engine or burner, in a tanker for generating a blanketing medium. The blanketing medium is selected from the group consisting of exhaust from a diesel engine, exhaust from a kerosene engine, exhaust from a methanol engine, exhaust from a gas oil engine, and exhaust from a gasoline engine. Additionally or alternatively, the blanketing medium is selected from the group consisting of flue gas from a diesel burner, flue gas from a kerosene burner, flue gas from a methanol burner, flue gas from a gasoline burner, and flue gas from a gas oil burner. Thus, the blanketing medium can include carbon dioxide, carbon monoxide, soot, $SO_x$, particulate contaminants and combinations thereof.

Another embodiment of the invention is a process for unloading methanol from a tanker. The process includes withdrawing methanol form a hold and replacing the volume of withdrawn methanol with a blanketing medium selected from the group consisting of exhaust from a diesel engine, exhaust from a kerosene engine, exhaust from a gas oil engine, exhaust from a gasoline engine, and exhaust from a methanol engine. Additionally or alternatively, the blanketing medium is selected from the group consisting of flue gas from a diesel burner, flue gas from a kerosene burner, flue gas from a methanol burner, flue gas from a gasoline burner, and flue gas from a gas oil burner. Thus, the blanketing medium may include carbon dioxide, carbon monoxide, soot, $SO_x$, particulate contaminants and combinations thereof.

Many non-methanol materials, such as crude and naphtha, leave hydrocarbon deposits on the inner surface of tanker holds after the material has been unloaded therefrom. Although a certain level of contaminants is acceptable for methanol destined for an oxygenate conversion reactor, ideally the level of hydrocarbon contaminants is minimized. Accordingly, the process for modifying a tanker to carry methanol also preferably includes cleaning the one or more holds with a cleaning agent to remove residual deposits formed by the non-methanol cargo. Ideally, the holds are first washed, e.g., hydroblasted at about 5,000 psi or mechanically washed at about 300 psi, with a first cleaning agent. The first cleaning agent preferably comprises water. The holds are then washed with a second cleaning agent comprising an emulsifier, such as GYRO Voyage Clean, a high solvency base emulsifier and cleaner with oil-sea water emulsification abilities. After being washed with the emulsifier, the emulsifier is rinsed from the holds with a water rinse. The first and second cleaning agents and the water rinse preferably are delivered to the tanker holds with a cleaning device such as a "Butterworth" system. If necessary, the internal surfaces of the holds may be hand washed and/or further chemically cleaned. The bottoms of the tanks may also be "mucked" of all residual hydrocarbons. All slops generated during the hold cleaning process above would need to be removed and disposed of properly. Approximately 800 tons of slops will be generated for a standard Aframax vessel in crude oil service. A wall test is preferably performed after the holds have been washed by the above-described process. The downtime for cleaning the holds is 1 to 3 weeks although no downtime would be incurred for cleaning if the tanker is cleaned during repositioning. Limited residual hydrocarbon contamination of the methanol will not significantly effect conversion or catalyst activity in an oxygenate conversion reaction system. Naphtha includes volatile light ($C_5$-) hydrocarbons and heavy ($C_6$+) hydrocarbons, which typically are low volatiles. Limited amounts of the light hydrocarbons may vaporize with the methanol and be transported to the reactor without significantly detrimental effects on conversion or catalyst activity. The methanol should vaporize away from the low-volatile heavy hydrocarbon contaminants in the vaporization system thereby separating the heavy hydrocarbons from the methanol feedstock destined for the oxygenate conversion reactor.

Unlike conventional methanol-carrying tanker holds, which are coated with a protective layer comprising zinc, holds in tankers designed to carry crude or naphtha are typically formed of uncoated carbon steel or coated with epoxy, which may break down in the presence of methanol thereby contaminating the methanol cargo. In accordance with the present invention, a methanol cargo is directed to the one or more uncoated tanker holds, zinc clad or, less desirably, epoxy-coated holds. Although the uncoated inner surface of the one or more tanker holds formed of carbon steel may impart discoloring contaminants such as rust (iron oxide) or leached metals to the methanol, it has been discovered that methanol stored in uncoated carbon steel holds may still be acceptable for use as a feedstock in an oxygenate conversion reaction system due to the advantages of oxygenate feedstock vaporization, discussed in detail above. Specifically, the discoloration caused by these contaminants is not an issue for an oxygenate conversion reaction system, which may also utilize uncoated carbon steel piping. Additionally, unlike conventional methanol-implementing processes such as MTBE and formaldehyde syntheses, methanol feed preheat and vaporization will vaporize methanol away from soot particles, rust and other non-volatiles contained in the feedstock. Similarly, although an epoxy coating layer may break down in the presence of methanol, methanol contamination therefrom does not render the methanol cargo unsatisfactory for use as a feedstock in an oxygenate conversion reaction system. Optionally, any existing epoxy coating layer is blasted off of the cargo holds thereby providing holds having uncoated inner surfaces.

Conventional crude and naphtha carrying tankers include cargo pumping systems comprising cargo pumps, which, when desired, pump the cargo out of the holds and off the tanker into on-shore storage tanks. The cargo pumps preferably include bronze or Ni—Al-Bronze casings, which are acceptable for use with a methanol cargo. However, carbon steel or stainless steel (SCS 14) internals and ductile cast iron casings are preferred. If fitted, mechanical seals are to be retrofitted with stainless steel components and buna N or EPDM elastomers. Control valves are submerged within each hold and are remotely operable to allow the cargo to be pumped out of the holds and through conduit lines to the on-shore storage tanks. These control valves are typically controlled hydraulically. The hydraulic system, which causes these valves to open, uses a hydraulic oil comprising hydrocarbons, which may leak into the holds causing hydrocarbon contamination of the methanol. In contrast, conventional methanol carrying tankers include a non-hydraulic mechanical or contained hydraulic mechanical means for removing methanol therefrom. Although hydrocarbon contamination may result from implementing a hydraulic control valve system with a methanol cargo, the resulting contaminated methanol is acceptable for use as a feedstock in an oxygenate conversion reaction system for the reasons discussed above regarding residual crude and naphtha hydrocarbon contamination of methanol. Nevertheless, the control valves optionally include one or more alcohol intolerant seals or gaskets, which may break down in the presence of methanol thereby causing control valve failure and significant hydrocarbon contamination. Thus, one embodiment of the invention includes replacing these alcohol intolerant seals and gaskets with alcohol resistant seals and gaskets. Ideally, all flange gaskets, slip type coupling joints, manhole and access hatch gaskets should be refit with materials suitable for methanol service. Preferably, the alcohol resistant seals and gaskets are formed of synthetic fiber with nitrile binder or an equivalent thereof.

Additionally, one or more preexisting ladders that provide for entry into the one or more holds may be coated or uncoated. Uncoated carbon steel ladders or ladders coated with epoxy, although subjecting the methanol cargo to contamination, will not render the methanol cargo unfit for use as a feedstock in an MTO reaction system. Optionally, the ladders are blasted to remove any coating thereon, or the ladders are retrofitted with SUS 316 stainless steel (minimum 22 mm square bar).

The process for modifying a crude or naphtha carrying tanker to carry methanol may be implemented in tankers of all sizes having varying ratings for dead weight tonnage (DWT). Preferably, the present invention is implemented in an Aframax size tanker rated at 75,000 to 125,000 DWT, although the invention may be implemented in a Suezmax tanker rated at 125,000 to 180,000 DWT, a very large crude carrier (VLCC) rated at 200,000 to 300,000 DWT or an ultra large crude carrier (ULCC) rated at 300,000 to 500,000 DWT. The invention also can be implemented in smaller tankers such as Panamax tankers rated at 45,000 to 65,000 DWT, Handy Size tankers rated at 20,000 to 30,000 DWT, or Handymax tankers rated at approximately 35,000 DWT. However, in these smaller tankers, a gas blanketing system is unnecessary. The total deadweight tonnage of the modified tanker may be at least 20,000; 35,000; 70,000; or at least 125,000 DWT.

Methanol that is stored in an unlined tank such as a conventional tanker hold will likely receive contaminants from the metal surfaces thereof. For example, rust (iron oxide) on the inner surfaces of the tank or hold may break away from the inner surface thereby contaminating the methanol with rust particles. These rust particles may cause the methanol to fail specification for Grade A or Grade AA methanol. More specifically, rust may cause the methanol to fail one or more of tests ASTM D1363, ASTM D1613, ASTM E346 and the visual appearance test for Grade A or AA methanol.

Also, the gas blanketing system may contribute to the contamination of methanol causing the methanol to fail specification for Grade A or Grade AA methanol. More specifically, soot from the blanketing medium may cause the methanol to fail one or more of test ASTM D1209 or the visual appearance test for Grade A or AA methanol. Additionally, $CO_2$ from the blanketing medium may cause the methanol to fail test ASTM D1363 for Grade A or AA methanol. The $CO_2$ may form carbonic acid in methanol, which can cause the methanol to fail test ASTM D1363 for Grade A or AA methanol. Additionally, $SO_x$ from the blanketing medium may cause the methanol to fail test ASTM D3961 for Grade A or AA methanol.

As indicated above, hydrocarbons from hydraulic oil or from deposits on the inner surface of the one or more of the holds may also contribute to the contamination of methanol causing the methanol to fail specification for Grade A or Grade AA methanol. More specifically, the hydrocarbons from the hydraulic oil or deposits from a previous non-methanol cargo may cause the methanol to fail one or more of tests ASTM D1722 and the visual appearance test for Grade A or AA methanol.

A tanker modified by the above-described invention may cause the contamination of methanol stored therein causing the methanol to not pass specification for Grades A or AA methanol. However, the present invention of converting methanol in a methanol-containing feedstock to light olefins, wherein the feedstock does not pass specification for Grade A or AA methanol, is not limited to a methanol-containing stream that has been unloaded from a tanker modified by the above-described processes.

In one embodiment, the invention is a process for forming light olefins. The process includes the steps of: (a) providing a feedstock comprising liquid methanol and a contaminant selected from the group consisting of $SO_x$, carbonic acid, and C5-hydrocarbons; (b) vaporizing at least a portion of the feedstock to form a vaporized feed stream, wherein the vaporized feed stream comprises vaporized methanol and at least a portion of the contaminant that was present in the feedstock; and (c) contacting the vaporized methanol with a catalyst in a reactor under conditions effective to convert at least a portion of the vaporized methanol to the light olefins. Optionally, the at least a portion of the contaminant comprises at least 0.001 weight percent, more preferably at least 0.01 weight percent, and most preferably at least 0.5 weight percent of the vaporized feed stream.

In another embodiment, the process of the invention includes the steps of: (a) providing a feedstock comprising liquid methanol and a contaminant selected from the group consisting of soot and rust; (b) vaporizing at least a portion of the feedstock to form a vaporized feed stream and a liquid stream, wherein the vaporized feed stream comprises vaporized methanol, and wherein the liquid stream comprises at least a portion of the contaminant that was present in the feedstock; and (c) contacting the vaporized methanol with a catalyst in a reactor under conditions effective to convert at least a portion of the vaporized methanol to the light olefins.

IV. Vaporization and Contaminant Removal

In another embodiment, the inventive process includes the step of providing a methanol-containing stream comprising liquid methanol and solid contaminants, wherein the methanol-containing stream does not pass specification for Grade AA methanol. The methanol-containing stream is heated under conditions effective to form a vaporized feed stream and a liquid stream, wherein the vaporized feed stream comprises vaporized methanol, and the liquid stream comprises the solid contaminants. The vaporized methanol contacts a catalyst under conditions effective to convert at least a portion of the vaporized methanol to light olefins.

The invention provides for increased efficiency in the removal of impurities/contaminants in the form of non-volatiles and/or low-volatiles from a feed stream as well as increased performance in maintaining efficient temperature and pressure of the oxygenate feed. A non-limiting list of exemplary non-volatile materials includes inorganic metals, salts, acids and bases, dirt, clay, sand, rust, soot, and mixtures and alloys of inorganic materials, e.g., catalyst fines. Such non-volatile materials can include organic compounds that exhibit a negligible vapor pressure at the conditions necessary to prepare a feed for the OTO conversion process. Examples of non-volatile and/or low-volatile organic compounds include asphaltenes, polymers, tars, coal, waxes, heavy oils, silicone oils and silicon polymers. Most of the non-volatile materials are either solids or viscous liquids at ambient conditions.

In addition to materials that exhibit negligible vapor pressure at the conditions necessary to prepare feed for the OTO conversion process, deleterious components that boil at temperatures significantly greater than the dominant oxygenate in the oxygenate feed may also be present in the oxygenate-containing feed. These low-volatile components may include crude oil, heavy naphthas, distillates and other petroleum fractions or blend stocks, as well as processed petroleum products, chemicals produced from petroleum products, lubricating oils, hydraulic oils, oil additives, as well as non-carbon based chemicals and inorganic chemicals including, but not limited to, those containing halogens. Many of the deleterious boilable components exhibit low vapor pressures at the conditions necessary to prepare feed for the OTO process and hence are either essentially non-volatile or low-volatile materials. Such non-volatile or low-volatile materials not only reduce or eliminate catalyst performance but can deposit on internal surfaces of the OTO conversion reactor as well as apparatuses situated downstream of the conversion reactor, e.g., the product recovery train. Many of these low-volatile or non-volatile contaminants in oxygenate-containing feeds are introduced from residual materials present in logistics systems such as ships, tanks, and pipelines employed in the storage and transportation of these feeds.

As used herein, the term "non-volatiles" means materials that have negligible vapor pressure at the OTO conversion temperature. These materials are neither sublimable nor boilable at OTO reaction conditions.

For present purposes, "low-volatiles" are defined as materials having a normal boiling point (at one atmosphere pressure) at least 100° F. (38° C.) higher than the normal boiling point of the dominant oxygenate component in the feed. "Volatiles" are defined herein as materials having a normal boiling point less than 100° F. (38° C.) higher than the normal boiling point of the dominant oxygenate component in the feed. For example, dodecane has a normal boiling point of about 421° F. (216° C.), and benzene has a normal boiling point of about 176° F. (80° C.). For the purposes of this invention, if methanol, which has a normal boiling point of about 148° F. (64° C.), is the dominant oxygenate, then dodecane is a low-volatile whereas benzene is a volatile. It will be recognized by those skilled in the art that detailed calculations or experiments are possible to estimate the approximate separation of all materials in the oxygenate feed that have measurable vapor pressures. These calculations can be used to estimate the efficiency of the invention.

According to one embodiment of the invention, a liquid-vapor disengaging drum receives an oxygenate-containing feed from at least one feed pre-heater and provides an effluent stream to one or more OTO reactors. Installed in a recycle loop for the drum is a heat exchange means comprising at least one heat exchanger, external to the vapor-liquid disengaging drum. In one embodiment, the heat exchanger means comprises a plurality of heat exchangers. The heat exchangers may be installed in series and/or in parallel relative to one another. In a particular embodiment, at least two heat exchangers are installed in parallel to each other in the recycle loop.

The specific heat exchanger employed can be any heat exchanger suitable for its purpose in the invention. For purposes of the invention, a heat exchanger is defined as a means for transferring heat from a heat source, such as a heat exchange fluid to a heated material, in this case the liquid effluent from the vapor-liquid disengaging drum, through a heat transferring medium located between the heat source and the heated material, such as metal. Heat transfer is thereby accomplished without physically contacting the heat source with the heated material.

Suitable heat exchangers for use herein can be selected from horizontal or vertical shell and tube exchangers configured for partial vaporization. In one embodiment, at least one exchanger comprises a circulating partial vaporizer where the circulation of the effluent liquid is either induced by at least one of: (i) mechanically pumping the effluent through the exchanger; or (ii) a thermosyphon where the weight or static head of the effluent liquid is greater than the weight or static head of the heat exchanged and partially vaporized effluent returning to the drum, thus inducing circulation through the exchanger. The circulating partial vaporizer can be situated externally to the vapor-liquid disengaging drum. Partial vaporizers utilizing mechanical pumps for circulation are preferred where the source of heat for the exchanger is either remote or in a location that does not permit the use of a thermosyphon.

Partial vaporizers can be configured to vaporize from about 5 to about 95 vol % of the circulating fluid, say, from about 20 to about 40 vol %, e.g., from about 30 to about 40 vol % of the circulating fluid. This level of vaporization generally prevents the deposition of non-volatiles and low-volatiles in the heat exchanger.

In one embodiment of the invention, heat is supplied to the heat exchanging means, e.g., a partial vaporizer, for exchange to the liquid oxygenatecontaining stream from the vapor-liquid disengaging drum from one or more of: an externally supplied steam, water from a quench operation, e.g., water used to quench an OTO conversion effluent stream (with attendant quenched products in the water), and/or the OTO conversion effluent itself. Operating plural heat exchangers located in parallel to one another provides desired flexibility. Flexibility in controlling heat exchange may further be provided by using more than one type of heat source to the heat exchanger means, e.g., providing each heat exchanger with a different type of heat source.

The heat exchanger means at least partially vaporizes the oxygenate-containing feed and delivers the at least partially vaporized feed to the vapor-liquid disengaging drum for separation into a vapor stream that exits the drum overhead and a liquid stream that optionally is combined with the preheated oxygenate feed entering the drum. The combined liquid in the drum circulates to the heat exchanging means and is at least partially vaporized again. The vapor-liquid disengaging drum approximates a theoretical single fractionation stage. A significant portion of the non-volatiles and low-volatiles remain in the liquid stream, with preferred concentrations being as that described above. As also described above, at least a portion of the liquid stream is separated from the vapor stream and recovered, the liquid stream that is separated being generally referred to as as liquid blowdown. The overall percentage by weight of the fresh oxygenate-containing feed (excluding recycle streams) vaporized in the drum is 100 wt % minus the percentage by weight of blowdown. In one embodiment, the total feed withdrawn from the drum as blowdown can range from about 1 to about 30 wt %, from about 1 to about 20 wt %, from about 1 to about 10 wt %, or from about 1 to about 5 wt %, based on total amount of feed sent to the drum. The amount of non-volatiles and low-volatiles in the vapor leaving the drum is related to the amount of unseparated liquid mist carried overhead with the vapor from the drum. The amount of non-volatiles and low-volatiles in the mist is inversely proportional to the weight percentage of blowdown. Thus, a measure of control is exercisable over the amount of non-volatiles and low-volatiles carried overhead with the vapor by increasing or decreasing the percentage of the total feed to the blowdown. The approximate concentration of non-volatiles or low-volatiles in the oxygenate liquid in the drum is subject to calculation. At some elevated concentration level in the liquid, the non-volatiles and/or low-volatiles begin to separate as a solid phase in the drum. The blowdown rate or weight percentage of fresh feed should be maintained at a sufficient level to avoid accumulations of a solid phase in the drum. Inasmuch as the properties of non-volatiles and low-volatiles can be expected to vary, a drum liquid analysis can be used to establish the blowdown weight percentage. A partial analysis of non-volatiles can be obtained using a conductivity probe, wherein ion concentration in an oxygenate liquid phase is related to conductivity. In one embodiment, the conductivity probe is installed online and may be used to control the blowdown rate.

Because the oxygenate feedstock normally is stored at ambient temperatures before use in the conversion process, the feedstock has to be heated prior to contacting the oxygenate conversion catalyst. However, by varying the heat content of the feedstock, the temperature at which the OTO conversion reactor is operated can be varied.

It is preferable to increase the heat content and/or the temperature of the feedstock through from one to about three intermediate stages, with each stage having a successively higher heat content. Many different streams in the oxygenate conversion process may be suitable sources for providing the necessary heat to increase heat contents. These streams include those derived from the heavy product fraction from the quench tower and the streams from the fractionator separating quench medium from other components. It should be pointed out that a stream may have a higher heat content after a heat exchange even though it has a lower temperature, primarily resulting from pressure changes and/or phase changes, such as vaporization of a liquid as may occur in an OTO conversion process. In one embodiment of the invention, the reactor feed temperature is further increased in a fourth stage of heat exchange on the vapor feed to the reactor. Steam can be used as a source of heat in this stage of heat exchange.

In accordance with one embodiment of the present invention, the preheated feedstream is then fed into at least one disengaging drum capable of maintaining proper pressure and temperature for separating impurities out of the oxygenate feed. Preferably only a single disengaging drum is employed inasmuch as a single feed vapor-liquid disengaging drum with multiple heat exchanger inputs is the least complex means to approach a single theoretical stage of fractionation sufficient to reject substantially all non-heavy hydrocarbon non-volatiles and many of the heavy hydrocarbon low-volatiles as well. The oxygenate feed then needs to be at least partially vaporized and contacted in a suitable oxygenate conversion reactor with the selected molecular sieve catalyst under process conditions effective to produce the desired olefins at an acceptable conversion level with desired selectivity.

The OTO catalyst is susceptible to poisons in the oxygenate-containing feed. At certain levels these poisons include rust, soot, metals, metal oxides, salts and heavy hydrocarbons. These poisons can incapacitate a catalyst, either temporarily or permanently, and therefore it is desirable to remove them completely from the oxygenate-containing feed to the OTO reactor.

In one embodiment of the invention, after contacting the oxygenate feedstock with the oxygenate conversion catalyst present in the OTO reactor, the oxygenate conversion reaction product effluent comprising olefin products is quenched directly by contacting a suitable quench medium in a quench tower. The compounds in the effluent stream that are gaseous under the quenching conditions are separated from the quench tower as a light product fraction for olefin product recovery and purification. The light product fraction comprises light olefins, dimethyl ether, methane, CO, $CO_2$, ethane, propane, and other minor components such as water and unreacted oxygenate feedstock. The compounds in the effluent stream that are liquid under quenching conditions, are separated from the quench tower as a heavy product fraction for heat recovery, and possible division into several fractions and separation of the quench medium. The heavy product fraction comprises byproduct water, a portion of the unreacted oxygenate feedstock (except those oxygenates that are gases under quenching conditions), a small portion of the oxygenate conversion byproducts, particularly heavy hydrocarbons ($C_6+$), and usually the bulk of the quench medium. Further details of such reactions may be found in U.S. Pat. No. 6,121,504, the entirety of which in incorporated herein by reference.

In one embodiment of the invention, where more than one vapor/liquid disengaging drum is utilized, it is preferable that a primary or controlling drum is used that has an independent source of steam. More preferably a secondary drums is maintained under at least the same pressure as the primary drum, and use of steam in the secondary drum is optional. The oxygenate vapor stream from the vapor/liquid disengaging drums is passed to the OTO reaction system, preferably through the primary drum.

V. Types of Molecular Sieves

The molecular sieves that are included in the catalyst or catalyst mixtures used in the conversion of oxygenates to olefins in this invention are preferably metalloaluminophosphate molecular sieves that have a molecular framework that include [$AlO_4$] and [$PO_4$] tetrahedral units, such as metal containing aluminophosphates (AlPO). In one embodiment, the metalloaluminophosphate molecular sieves include [$AlO_4$], [$PO_4$] and [$SiO_4$] tetrahedral units, such as silicoaluminophosphates (SAPO).

Various silicon, aluminum, and phosphorus based molecular sieves and metal-containing derivatives thereof have been described in detail in numerous publications including for example, U.S. Pat. No. 4,567,029 (MeAPO where Me is Mg, Mn, Zn, or Co), U.S. Pat. No. 4,440,871 (SAPO), European Patent Application EP-A-0 159 624 (ELAPSO where El is As, Be, B, Cr, Co, Ga, Ge, Fe, Li, Mg, Mn, Ti or Zn), U.S. Pat. No. 4,554,143 (FeAPO), U.S. Pat. Nos. 4,822,478, 4,683,217, 4,744,885 (FeAPSO), EP-A-0 158 975 and U.S. Pat. No. 4,935,216 (ZnAPSO, EP-A-0 161 489 (CoAPSO), EP-A-0 158 976 (ELAPO, where EL is Co, Fe, Mg, Mn, Ti or Zn), U.S. Pat. No. 4,310,440 (AlPO4), EP-A0 158 350 (SENAPSO), U.S. Pat. No. 4,973,460 (LiAPSO), U.S. Pat. No. 4,789,535 (LiAPO), U.S. Pat. No. 4,992,250 (GeAPSO), U.S. Pat. No. 4,888,167 (GeAPO), U.S. Pat. No. 5,057,295 (BAPSO), U.S. Pat. No. 4,738,837 (CrAPSO), U.S. Pat. Nos. 4,759,919, and 4,851,106 (CrAPO), U.S. Pat. Nos. 4,758,419, 4,882,038, 5,434,326 and 5,478,787 (MgAPSO), U.S. Pat. No. 4,554,143 (FeAPO), U.S. Pat. No. 4,894,213 (AsAPSO), U.S. Pat. No. 4,913,888 (AsAPO), U.S. Pat. Nos. 4,686,092, 4,846,956 and 4,793,833 (MnAPSO), U.S. Pat. Nos. 5,345,011 and 6,156,931 (MnAPO), U.S. Pat. No. 4,737,353 (BeAPSO), U.S. Pat. No. 4,940,570 (BeAPO), U.S. Pat. Nos. 4,801,309, 4,684,617 and 4,880,520 (TiAPSO), U.S. Pat. Nos. 4,500, 651, 4,551,236 and 4,605,492 (TiAPO), U.S. Pat. No. 4,824, 554, 4,744,970 (CoAPSO), U.S. Pat. No. 4,735,806 (GaAPSO) EP-A-0 293 937 (QAPSO, where Q is framework oxide unit [QO2]), as well as U.S. Pat. Nos. 4,567,029, 4,686,093, 4,781,814, 4,793,984, 4,801,364, 4,853,197, 4,917,876, 4,952,384, 4,956,164, 4,956,165, 4,973,785, 5,241,093, 5,493,066 and 5,675,050, all of which are herein fully incorporated by reference. Other molecular sieves include those described in R. Szostak, Handbook of Molecular Sieves, Van Nostrand Reinhold, New York, N.Y. (1992), which is herein fully incorporated by reference.

The more preferred molecular sieves are SAPO molecular sieves, and metal-substituted SAPO molecular sieves. Suitable metal substituents are alkali metals of Group IA of the Periodic Table of Elements, an alkaline earth metals of Group IIA of the Periodic Table of Elements, a rare earth metals of Group IIIB, including the Lanthanides: lanthanum, cerium, praseodymium, neodymium, samarium, europium, gadolinium, terbium, dysprosium, holmium, erbium, thulium, ytterbium and lutetium; and scandium or yttrium of the Periodic Table of Elements, transition metals of Groups IVB, VB, VIB, VIIB, VIIIB, and IB of the Periodic Table of Elements and mixtures of any of these metal species. In one embodiment, the metal is selected from the group consisting of Co, Cr, Cu, Fe, Ga, Ge, Mg, Mn, Ni, Sn, Ti, Zn and Zr, and mixtures thereof. The metal atoms may be inserted into the framework of a molecular sieve through a tetrahedral unit, such as [MeO2], and carry a net charge depending on the valence state of the metal substituent. For example, in one embodiment, when the metal substituent has a valence state of +2, +3, +4, +5, or +6, the net charge of the tetrahedral unit is between −2 and +2.

In one embodiment, the metalloaluminophosphate molecular sieve is represented, on an anhydrous basis, by the formula:

$$mR:(M_xAl_yP_z)O_2$$

wherein R represents at least one templating agent, preferably an organic templating agent; m is the number of moles of R per mole of $(M_xAl_yP_z)O_2$ and m has a value from 0 to 1, preferably 0 to 0.5, and most preferably from 0 to 0.3; x, y, and z represent the mole fraction of Al, P and M as tetrahedral oxides, where M is a metal selected from the group consisting of Group IA, IIA, IB, IIIB, IVB, VB, VIB, VIIB, VIIIB and Lanthanide's of the Periodic Table of Elements. Preferably M is one or more metals selected from the group consisting of Si, Co, Cr, Cu, Fe, Ga, Ge, Mg, Mn, Ni, Sn, Ti, Zn and Zr. In an embodiment, m is greater than or equal to 0.2, and x, y and z are greater than or equal to 0.01. In another embodiment, m is greater than 0.1 to about 1, x is greater than 0 to about 0.25, y is in the range of from 0.4 to 0.5, and z is in the range of from 0.25 to 0.5, more preferably m is from 0.15 to 0.7, x is from 0.01 to 0.2, y is from 0.4 to 0.5, and z is from 0.3 to 0.5.

In one embodiment of the invention, the metalloaluminophosphate molecular sieves are silicoaluminophosphate molecular sieves, containing silicon and aluminum. In general, lower Si/Al ratios lead to lower deactivation rates and higher ACIs for a given set of conditions. However, higher Si/Al ratios can be used under the appropriate conditions of temperature, water partial pressure and time of contact with water. Desirably, the metalloaluminophosphate molecular sieves of this invention are silicoaluminophosphate molecular sieves that contain Si and Al, at a Si/Al ratio of not greater than about 0.5, preferably not greater than about 0.3, more preferably not greater than about 0.2, still more preferably not greater than about 0.15, and most preferably not greater than about 0.1. In another embodiment, the Si/Al ratio is sufficiently high to allow for increased catalytic activity of the molecular sieve. Preferably, the metalloaluminophosphate molecular sieves are silicoaluminophosphate molecular sieves that contain Si and Al at a ratio of at least about 0.005, more preferably at least about 0.01, and most preferably at least about 0.02.

Non-limiting examples of SAPO and AlPO molecular sieves useful herein include one or a combination of SAPO-5, SAPO-8, SAPO-11, SAPO-16, SAPO-17, SAPO-18, SAPO-20, SAPO-31, SAPO-34, SAPO-35, SAPO-36, SAPO-37, SAPO-40, SAPO-41, SAPO-42, SAPO-44, SAPO-47, SAPO-56, AlPO-5, AlPO-11, AlPO-18, AlPO-31, AlPO-34, AlPO-36, AlPO-37, AlPO-46, and metal containing molecular sieves thereof. Of these, particularly useful molecular sieves are one or a combination of SAPO-18, SAPO-34, SAPO-35, SAPO-44, SAPO-56, AlPO-18, AlPO-34 and metal containing derivatives thereof, such as one or a combination of SAPO-18, SAPO-34, AlPO-34, AlPO-18, and metal containing derivatives thereof, and especially one or a combination of SAPO-34, AlPO-18, and metal containing derivatives thereof.

In an embodiment, the molecular sieve is an intergrowth material having two or more distinct crystalline phases within one molecular sieve composition. In particular, intergrowth molecular sieves are described in U.S. Patent Application Publication No. 2002-0165089 and International Publication No. WO 98/15496, published Apr. 16, 1998, both of which are herein fully incorporated by reference. For example, SAPO-18, AlPO-18 and RUW-18 have an AEI framework-type, and SAPO-34 has a CHA framework-type. Thus, the molecular sieve used herein may comprise at least one intergrowth phase of AEI and CHA framework-types, especially where the ratio of CHA framework-type to AEI framework-type, as determined by the DIFFaX method disclosed in U.S. Patent Application Publication No. 2002-0165089, is greater than 1:1.

Various methods for synthesizing molecular sieves or modifying molecular sieves are described in U.S. Pat. No. 5,879,655 (controlling the ratio of the templating agent to phosphorus), U.S. Pat. No. 6,005,155 (use of a modifier without a salt), U.S. Pat. No. 5,475,182 (acid extraction), U.S. Pat. No. 5,962,762 (treatment with transition metal), U.S. Pat. Nos. 5,925,586 and 6,153,552 (phosphorus modified), U.S. Pat. No. 5,925,800 (monolith supported), U.S. Pat. No. 5,932,512 (fluorine treated), U.S. Pat. No. 6,046,373 (electromagnetic wave treated or modified), U.S. Pat. No. 6,051,746 (polynuclear aromatic modifier), U.S. Pat. No. 6,225,254 (heating template), PCT WO 01/36329 published May 25, 2001 (surfactant synthesis), PCT WO 01/25151 published Apr. 12, 2001 (staged acid addition), PCT WO 01/60746 published Aug. 23, 2001 (silicon oil), U.S. Patent Application Publication No. 20020055433 published May 9, 2002 (cooling molecular sieve), U.S. Pat. No. 6,448,197 (metal impregnation including copper), U.S. Pat. No. 6,521,562 (conductive microfilter), and U.S. Patent Application Publication No. 20020115897 published Aug. 22, 2002 (freeze drying the molecular sieve), which are all herein fully incorporated by reference.

In general, molecular sieve catalyst is also referred to as formulated molecular sieve catalyst. The formulated catalyst optionally contains binder and matrix materials. Conventionally, formulated catalyst is made by mixing together molecular sieve crystals (which includes template) and a liquid, optionally with matrix material and/or binder, to form a slurry. The slurry is then dried (i.e., liquid is removed), without completely removing the template from the molecular sieve. Since this dried molecular sieve catalyst includes template, it has not been activated, and is considered a preformed catalyst. However, the preformed catalyst must be activated before use, and this invention provides appropriate methods to protect the activated catalyst from significant deactivation.

The liquid used to form the slurry can be any liquid conventionally used in formulating molecular sieve catalysts. Non-limiting examples of suitable liquids include water, alcohol, ketones, aldehydes, esters, or a combination thereof. Water is a preferred liquid.

Matrix materials are optionally included in the slurry used to make the formulated molecular sieve catalyst of this invention. Such materials are typically effective as thermal sinks assisting in shielding heat from the catalyst composition, for example, during regeneration. They can further act to densify the catalyst composition, increase catalyst strength such as crush strength and attrition resistance, and to control the rate of conversion in a particular process. Non-limiting examples of matrix materials include one or more of: rare earth metals, metal oxides including titania, zirconia, magnesia, thoria, beryllia, quartz, silica or sols, and mixtures thereof; for example, silica-magnesia, silica-zirconia, silica-titania, silica-alumina and silica-alumina-thoria.

In one embodiment, matrix materials are natural clays, such as those from the families of montmorillonite and kaolin. These natural clays include kaolins known as, for example, Dixie, McNamee, Georgia and Florida clays. Non-limiting examples of other matrix materials include: halloysite, kaolinite, dickite, nacrite, or anauxite. Optionally, the matrix material, preferably any of the clays, are calcined, acid treated, and/or chemical treated before being used as a slurry component. Under the optional calcination treatment, the matrix material will still be considered virgin material as long as the material has not been previously used in a catalyst formulation.

In a particular embodiment, the matrix material is a clay or a clay-type composition, preferably a clay or clay-type composition having a low iron or titania content, and most preferably the matrix material is kaolin. Kaolin has been found to form a pumpable, high solid content slurry; it has a low fresh surface area, and it packs together easily due to its platelet structure.

Binders are also optionally included in the slurry used to make the formulated molecular sieve catalysts of this invention. Such materials act like glue, binding together the molecular sieve crystals and other materials, to form a formulated catalyst composition. Non-limiting examples of binders include various types of inorganic oxide sols such as hydrated aluminas, silicas, and/or other inorganic oxide sols. In one embodiment of the invention, the binder is an alumina-containing sol, preferably aluminium chlorohydrate. Upon calcining, the inorganic oxide sol, is converted into an inorganic oxide matrix component, which is particularly effective in forming a hardened molecular sieve catalyst composition. For example, an alumina sol will convert to an aluminium oxide matrix following heat treatment.

The molecular sieve crystals are mixed with liquid, and the optional matrix material and/or binder, using conventional techniques to form a slurry. The components can be mixed in any order, and the mixture is thoroughly stirred to form the slurry. The more thorough the stirring, the better the consistency of the slurry.

Liquid is removed from the slurry containing the molecular sieve crystals to form a preformed molecular sieve catalyst. Preferably, the slurry is fed to a forming unit that produces the preformed molecular sieve catalyst composition. The forming unit may be any conventional unit, such as a spray dryer, pelletizer, extruder, etc. In a preferred embodiment, the forming unit is spray dryer, which removes water from the slurry by a heating or drying process. Preferably, the forming unit is maintained at a temperature sufficient to remove a majority of the liquid from the slurry.

The molecular sieve material is activated by removing the template from the preformed molecular sieve catalyst composition so as to expose the active catalytic sites to the environment. The template can be removed by any conventional technique, including for example by elution methods or by heating such as calcining. The molecular sieve crystals themselves can be activated for immediate catalytic use or for storing or transporting prior to use. However, it is preferred that the molecular sieves be formulated into a preformed catalyst, then activated by calcining. The formulated product generally provides the most effective particle size and hardness for commercial scale equipment.

VI. Converting Oxygenates to Products

This invention relates to an OTO reaction system or process. The most preferred OTO process is generally referred to as a gas-to-olefins (GTO) or alternatively an MTO reaction process. In an MTO reaction process, methanol in a methanol-containing feedstock is converted in the presence of a molecular sieve catalyst composition into one or more olefins, preferably and predominantly, ethylene and/or propylene, often referred to as light olefins.

The preferred MTO process and reaction conditions will now be described in more detail. Preferably, the conditions in the MTO reactor including the pressure, temperature, weight hourly space velocity (WHSV), etc., are conducive to converting the methanol to light olefins, as discussed below. Typically, molecular sieve catalysts are used to convert oxygenate compounds to light olefins. Silicoaluminophosphate (SAPO) molecular sieve catalysts are particularly desirable in such conversion processes, because they are highly selective in the formation of ethylene and propylene.

The various feedstocks discussed above, particularly a feedstock containing an oxygenate, more particularly a feedstock containing an alcohol, are converted primarily into one or more olefins. The olefins or olefin monomer(s) produced from the feedstock typically have from about 2 to about 30 carbon atoms, preferably from about 2 to about 8 carbon atoms, more preferably from about 2 to about 6 carbon atoms, still more preferably from about 2 to about 4 carbons atoms, and most preferably ethylene and/or propylene.

Non-limiting examples of olefin monomers include ethylene, propylene, butene-1, pentene-1, 4-methyl-pentene-1, hexene-1, octene-1 and decene-1, preferably ethylene, propylene, butene-1, pentene-1, 4-methyl-pentene1, hexene-1, octene-1 and isomers thereof. Other olefin monomers include unsaturated monomers, diolefins having 4 to 18 carbon atoms, conjugated or nonconjugated dienes, polyenes, vinyl monomers and cyclic olefins.

In the most preferred embodiment, the feedstock, preferably of one or more oxygenates, is converted in the presence of a molecular sieve catalyst composition into one or more olefins having from about 2 to about 6 carbons atoms, preferably from about 2 to about 4 carbon atoms. Most preferably, the olefins, alone or in combination, are converted from a feedstock containing an oxygenate, preferably an alcohol, most preferably methanol, to the preferred olefins ethylene and/or propylene.

The feedstock, in one embodiment, contains one or more diluents, typically used to reduce the concentration of the feedstock. The diluents are generally non-reactive to the feedstock or molecular sieve catalyst composition. Non-limiting examples of diluents include helium, argon, nitrogen, carbon monoxide, carbon dioxide, water, essentially non-reactive paraffins (especially alkanes such as methane, ethane, and propane), essentially non-reactive aromatic compounds, and mixtures thereof. The most preferred diluents are water and nitrogen, with water being particularly preferred. In other embodiments, the feedstock does not contain any diluent.

The diluent may be used either in a liquid or a vapor form, or a combination thereof. The diluent is either added directly to the feedstock entering into the reactor or added directly into the reactor, or added with the molecular sieve catalyst composition. In one embodiment, the amount of diluent in the feedstock is in the range of from about 1 to about 99 mole percent based on the total number of moles of the feedstock and diluent, preferably from about 1 to about 80 mole percent, more preferably from about 5 to about 50, most preferably from about 5 to about 25. In one embodiment, other hydrocarbons are added to the feedstock either directly or indirectly, and may include olefin(s), paraffin(s), aromatic(s) (see for example U.S. Pat. No. 4,677,242) or mixtures thereof, preferably propylene, butylene, pentylene, and other hydrocarbons having 4 or more carbon atoms, or mixtures thereof.

The process for converting a feedstock, especially a feedstock containing one or more oxygenates, in the presence of a molecular sieve catalyst composition of the invention, is carried out in a reaction process in a reactor, where the process is a fixed bed process, a fluidized bed process (optionally a turbulent bed process), preferably a continuous fluidized bed process, and most preferably a continuous high velocity fluidized bed process.

The reaction processes may take place in a variety of catalytic reactors such as hybrid reactors that have a dense bed or fixed bed reaction zones and/or fast fluidized bed reaction zones coupled together, circulating fluidized bed reactors, riser reactors, and the like. Suitable conventional reactor types are described, for example, in U.S. Pat. No. 4,076,796, U.S. Pat. No. 6,287,522 (dual riser), and *Fluidization Engineering*, D. Kunii and O. Levenspiel, Robert E. Krieger Publishing Company, New York, N.Y. 1977, which are all herein fully incorporated by reference. Dual riser reactors or other reactor designs optionally include a plurality of feed introduction nozzles.

The preferred reactor type is a riser reactor generally described in *Riser Reactor, Fluidization and Fluid-Particle Systems*, pages 48 to 59, F. A. Zenz and D. F. Othmer, Reinhold Publishing Corporation, New York, 1960, and U.S. Pat. No. 6,166,282 (fast-fluidized bed reactor), and U.S. patent application Ser. No. 09/564,613, filed May 4, 2000 (multiple riser reactor), which are all herein fully incorporated by reference.

In one embodiment, the amount of fresh feedstock fed separately or jointly with a vapor feedstock to a reactor system is in the range of from about 0.1 weight percent to about 95 weight percent, preferably from about 10 weight percent to about 90 weight percent, more preferably from about 50 weight percent to about 85 weight percent, based on the total weight of the feedstock including oxygenate recycle and any diluent contained therein. The liquid and vapor feedstocks are preferably the same composition, or contain varying proportions of the same or different feedstock with the same or different diluent.

The conversion temperature employed in the conversion process, specifically within the reactor system, is in the range of from about 200° C. (392° F.) to about 1000° C. (1832° F.), preferably from about 250° C. (392° F.) to about 800° C. (1472° F.), more preferably from about 250° C. (482° F.) to about 750° C. (1382° F.), yet more preferably from about 300° C. (572° F.) to about 650° C. (1202° F.), yet even more preferably from about 350° C. (662° F.) to about 600° C. (1112° F.), and most preferably from about 350° C. (662° F.) to about 550° C. (1022° F.).

The conversion pressure employed in the conversion process, specifically within the reactor system, varies over a wide range including autogenous pressure. The conversion pressure is based on the partial pressure of the feedstock exclusive of any diluent therein. Typically the conversion pressure employed in the process is in the range of from about 0.1 kPaa (0.015 psia) to about 5 MPaa (730 psia), preferably from about 5 kPaa (0.73 psia) to about 1 MPaa (145 psia), and most preferably from about 20 kPaa (2.9 psia) to about 500 kPaa (72.5 psia).

The weight hourly space velocity (WHSV), particularly in a process for converting a feedstock containing one or more oxygenates in the presence of a molecular sieve catalyst composition within a reaction zone, is defined as the total weight of the feedstock, excluding any diluents, that is fed to the reaction zone per hour per weight of molecular sieve in the molecular sieve catalyst composition in the reaction zone. The WHSV is maintained at a level sufficient to keep the catalyst composition in a fluidized state within the reactor.

Typically, the WHSV ranges from about 1 $hr^{-1}$ to about 5000 $hr^{-1}$, preferably from about 2 $hr^{-1}$ to about 3000 $hr^{-1}$, more preferably from about 5 $hr^{-1}$ to about 1500 $hr^{-1}$, and most preferably from about 10 $hr^{-1}$ to about 1000 $hr^{-1}$. In one preferred embodiment, the WHSV is greater than 20 $hr^{-1}$, preferably the WHSV for conversion of a feedstock containing methanol, dimethyl ether, or both, is in the range of from about 20 $hr^{-1}$ to about 300 $hr^{-1}$.

The superficial gas velocity (SGV) of the feedstock including diluent and reaction products within the reactor system is preferably sufficient to fluidize the molecular sieve catalyst composition within a reaction zone in the reactor. The SGV in the process, particularly within the reactor system, more particularly within the one or more riser reactors, is at least about 0.1 meter per second (m/sec), preferably greater than about 0.5 m/sec, more preferably greater than about 1 m/sec, even more preferably greater than about 2 m/sec, yet even more preferably greater than about 3 m/sec, and most preferably greater than about 4 m/sec.

VII. Detailed Descriptions of Various Embodiments of the Invention

Referring to FIG. 1, one aspect of the invention and a number of the preferred embodiments are shown. In particular, FIG. 1 shows a two stage vaporization process with the first heating stage being represented by a combination of heat exchangers 48, 50, 52 and vapor-liquid disengaging drum 14, and a second stage being represented by a combination of heat exchanger 78 and condensate stripper 74. Oxygenate feed is heated by heat exchangers 48, 50, 52 to form a vapor stream and a liquid stream. The vapor stream is separated from the liquid stream in vapor-liquid disengaging drum 14, and is sent through a line 30 to contact metalloaluminophosphate molecular sieve to convert the oxygenate in the vapor to olefin product. Liquid from the vapor-liquid disengaging drum is sent to the condensate stripper 74, which is further heated by the heat exchanger 78 to vaporize additional oxygenate remaining in the liquid. A significant portion of the vapor stream formed in the condensate stripper 74 is sent through a line 89 to combine with the vapor in the first heating stage, and the combined vapor streams are sent through the line 30 to contact the metalloaluminophosphate molecular sieve to convert the oxygenate in the vapor to olefin product. A final liquid stream exits the condensate stripper 74 and is sent through a line 81 to be discarded, for example, by sending to a waste collection or treatment system. The combined vapor stream is very low in contaminant level, with a substantial quantity of contaminants, particularly metals, being found in the final liquid stream that is discarded.

Referring to FIG. 1 in greater detail, an oxygenate-containing feed 2 which contains impurities, which if not at least partially removed, can deleteriously deposit on catalyst and/or on the internal surfaces throughout the apparatus of the process. One or more pumps 6 can be used to maintain or facilitate flow of the feed. The oxygenate-containing feed 2 is heated by one or more feed preheaters 8, 10 and 12 which may be arranged serially and/or in parallel, prior to being fed into a vapor-liquid disengaging drum 14 via vapor-liquid disengaging drum inlet 16.

The vapor-liquid disengaging drum 14 is the primary location where non-volatiles and/or low volatiles present in the oxygenate-containing feed are separated from volatiles, e.g., materials that are distillable and/or sublimable under the conditions used to prepare OTO feeds. The disengaging drum 14 contains a boilable fluid medium such as an oxygenate compound which is used as a heat sink to control the temperature within the vapor-liquid disengaging drum. The drum is operated so as to maintain the oxygenate feed at a predetermined temperature and pressure. The temperature and pressure levels are maintained sufficient to provide an at least partially vaporized effluent stream (or phase) and an at least partially liquid stream (or phase).

The at least partially vaporized effluent stream is passed through drum outlet 18, optionally through an optional wash column demister 20 comprising packing and demister screens 22 and 24 and having an upper inlet 26 for a wash column demister liquid oxygenate reflux 28 and eventually fed as vapor via line 30 into an OTO reactor, not shown, and/or directed through condenser 32 to an upper inlet 34 of condenser drum 36 having a bottoms outlet 37 through which liquid condensed oxygenate is passed to pump 38 for transmission to condenser drum recycle inlet 40, to wash column demister 20 as a demister wash column wash via reflux 28, and/or to an OTO reactor via line 42. Thus, in one embodiment of the invention, a liquid feed is fed into the OTO reactor. This liquid feed should be free of non-volatiles and, preferably, low-volatiles and kept close to its vapor point. The liquid feed is used to control the temperature in the OTO reactor and the proportion of vapor to liquid feed used is dependent on the OTO reactor conditions as described above. The wash column demister 20 will further remove any entrained non-volatiles.

An at least partially liquid stream (or phase) from the vapor-liquid disengaging drum is passed through a vapor-liquid disengaging drum liquid stream outlet 44 via line 46 to a heat exchanger means. The heat exchanger means can comprise a plurality of heat exchangers 48, 50 and 52, respectively, installed in parallel inlet lines 54, 56 and 58, respectively. Heat is thus added to the at least partially liquid stream and a heated at least partially vapor stream removed from the heat exchangers via lines 60, 62 and 64, thence through line 66 to a second inlet 68 to the vapor-liquid disengaging drum 14. Heat is supplied to the partial vaporizers 48, 50 and 52, via hot OTO reactor effluent 49, steam 51, and/or hot quench liquid 53 resulting from quenching OTO reactor effluent, e.g., using quench water. Heat input to the heat exchangers is controlled so as to provide a heat exchanged vapor phase oxygenate-containing stream of sufficient heat content as vaporized feed via drum outlet 18 for OTO reactor requirements.

In one aspect of the invention, the vapor phase is removed through drum outlet 18. The vapor phase is free of non-volatiles and, preferably, low-volatiles except for liquid phase mist carried with the vapor phase through outlet 18. The majority of the non-volatiles and low-volatiles accumulate in the liquid phase and can be removed from the disengaging drum via outlet 70. These non-volatiles and low-volatiles may be disposed of in a variety of useful manners known in the art. In one embodiment volatiles trapped in the liquid are removed by conveying the liquid via pump 72 to the top of condensate stripper 74 via line 75. Alternatively, the liquid can be conveyed to the condensate stripper through intermediate condensate stripper inlet 76, particularly in those instances where an alternate source of reflux is made available to the top of the condensate stripper as discussed below. The condensate stripper 74 is heated by a condensate stripper bottoms heat exchanger 78 wherein heat is added to at least a portion of the bottoms taken from condensate stripper outlet 80 via line 82. The heated bottoms are returned to the condensate stripper via line 84. The bottoms, which contain water, heavy hydrocarbons, non-volatiles and low-volatiles, may be removed via line 81 to a disposal or recycle system, not shown, which may include a water treatment plant. In one embodiment, the solids and heavy hydrocarbons in the liquid stream can be directed to heavy oil removal and separation systems included with the aforementioned quench systems used to treat oxygenate to olefins reactor effluent.

Condensate containing oxygenates, e.g., methanol and water, such as that provided by quenching an OTO reactor effluent as discussed above can be separately added to condensate stripper 74 via intermediate condensate stripper inlet 86. Condensate stripper overhead is removed from the condensate stripper by line 88 and recycled to the vapor-liquid disengaging drum 14 through vapor-liquid disengaging drum inlet 90. In one embodiment, at least a portion of the overhead from line 88 is directed through line 92 through condenser 94 and to a condensate stripper overhead condenser drum 96, which separates out non-condensables from condensable liquids. This condensate stripper overhead condenser drum 96 is separate from the vapor-liquid disengaging drum 14. A vapor-containing stream is taken off the condensate stripper overhead condenser drum 96 through line 98, and a liquid-containing stream is taken via line 100 and preferably is directed by reflux pump 102 to i) the top of condensate stripper 74 via line 104 and/or ii) an OTO reactor inlet via lines 105 and 42. Regulating the flow of these liquid-containing streams via lines 105 and/or 42 can be used to control temperature in the OTO reactor. These liquid-containing streams that contain extremely low levels of at least low-volatile contaminants are thus well-suited as feeds to the reactor. The vapor-containing stream can be subsequently flared or utilized as fuel. In an alternate embodiment, at least a portion of the condensate stripper overhead is directed via line 89 to vaporized effluent in line 30 and introduced into the OTO reactor. This is particularly suited where reflux to the condensate stripper 74 is provided by an alternate oxygenate-containing stream such as blowdown from the vapor-liquid disengaging drum 14.

In a particular embodiment of the present invention, an OTO reactor effluent, e.g., reactor effluent 49 is taken via line 106 to a reactor effluent quench unit 108 whose bottoms can be directed to condensate stripper 74 via line 110 and intermediate condensate stripper inlet 86. Quench unit overhead containing olefins is taken via line 112 to initial olefin recovery unit 114 and thence via line 116 to a product recovery wash system 118, e.g., a column, to which water or oxygenate-containing wash is fed via line 120 to remove water and/or oxygenates. Typically, an oxygenate-containing wash can be derived from oxygenate feed, condensate, boiler feed water, process water or product oxygenates, as well as other suitable sources. The oxygenates in the wash extract may be recovered and purified as feed for the OTO reactor. Wash extract is removed via line 124 and directed to quench tower 108 or condensate stripper 74. Washed overhead is taken via line 126 to additional olefins recovery unit 128 to form one or more final product streams, not shown.

Figure 2:
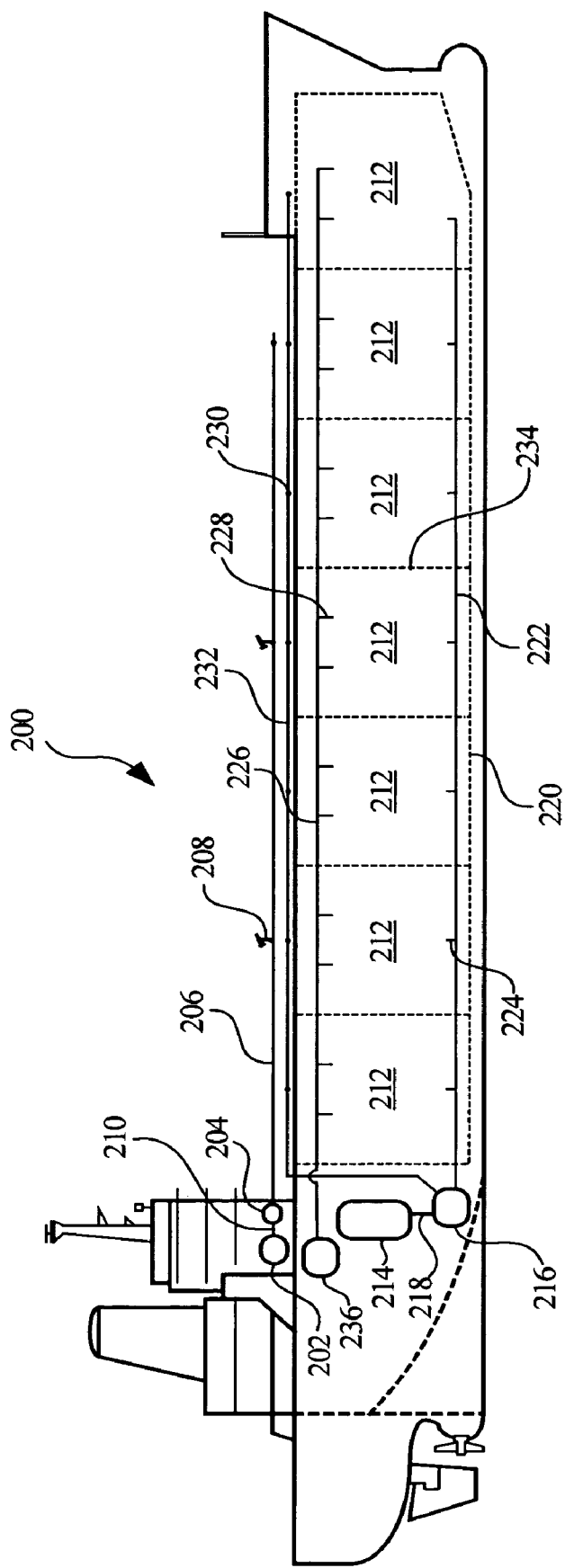
FIG. 2 illustrates a partial cross-sectional side view of a tanker that has been modified to carry methanol destined for a methanol-to-olefin reaction system.

FIG. 2 illustrates a tanker, generally designated 200, that has been modified by the above-described process. Tanker 200 includes a plurality of uncoated holds 212 for storing methanol. Each hold includes side surfaces 234 defining the side limits thereof and separating a hold from an adjacent hold. Each hold also includes a bottom surface 220 defining the bottom limit thereof. The side surface 234 and the bottom surface 220 are preferably formed of an uncoated material such as carbon steel.

The modified tanker 200 includes a fire suppression system adapted to provide an alcohol-resistant fire suppression agent to the one or more holds 212 or the tanker deck. The fire suppression system includes a fire suppression agent storage tank 202, which stores the fire suppression agent. The storage tank 202 includes a pump line 210 in fluid communication with pump 204. In the event of a fire in one or more of the holds or on the deck of the tanker 200, the pump 204 is activated to pump the alcohol-resistant fire suppression agent from the storage tank 202 through the pump line 210 and pump 204 and into fire suppression header line 206. Header line 206 directs the fire suppression agent to one or more, preferably a plurality of, fire suppression agent outlets 208. FIG. 2 illustrates three fire suppression agent outlets 208, each of which is an aimable turret. In the event of a fire, a remote control mechanism or an individual directs one or more of the aimable turrets towards the fire in order to extinguish it.

FIG. 2 also illustrates a cargo pumping mechanism adapted to pump the methanol cargo off of the ship or to circulate the methanol through the holds 212. The cargo pumping mechanism includes a methanol intake line 222, which extends longitudinally through the tanker holds 212. Although the intake line 222 is illustrated internally with respect to the holds 212, the intake line could be oriented externally to the holds 212. The intake line 222 includes a plurality of methanol inlets 224, each inlet being adapted to receive methanol from a respective hold. FIG. 2 illustrates one methanol inlet 224 per hold 212 although a plurality of inlets 224 may be oriented with respect to a single hold 212. Pump motor 214 operates on motor shaft 218 to power cargo pump 216. Cargo pump 216 creates a pressure drop on methanol intake line 222 thereby causing methanol to be supplied thereto through methanol inlet 224. The methanol received in methanol inlet 224 flows through methanol intake line 222, through pump 216 and into methanol discharge line 232. Methanol discharge line 232 is also longitudinally oriented with respect to tanker 200 and extends over the top of the holds 212. The discharge line 232 includes a plurality of methanol outlets 230, which optionally are in fluid connection with a series of external conduit lines for unloading the methanol from tanker 200. Alternatively, the outlets 230 may extend inside each enclosed hold 212 and discharge the methanol back into the holds 212 thereby providing for cargo circulation between the holds.

A gas blanketing system is also shown including a gas blanket medium generator 236. The gas blanket medium generator 236 may be a gasoline, kerosene, methanol, or diesel burning engine or an inert gas generator such as a nitrogen generator. The gas blanketing medium from gas blanket medium generator 236 is directed through gas blanket conduit line 226, which extends longitudinally over each of the enclosed holds 212. The conduit line 226 directs the gas blanketing medium to a plurality of blanket outlets 228, each of which extends inside a respective enclosed hold 212. In this manner the gas blanketing medium is directed to each of the holds 212. Two blanket outlets 228 are shown in FIG. 2 for each hold 212 although each hold may have a single blanket outlet or more than two blanket outlets.

Having now fully described the invention, it will be appreciated by those skilled in the art that the invention may be performed within a wide range of parameters within what is claimed, without departing from the spirit and scope of the invention.

What is claimed is:

1. A process for removing metalloaluminophosphate molecular sieve contaminants from an oxygenate feed and converting the oxygenate in the feed to olefin product, comprising the steps of:
   a) heating the oxygenate feed to form a vapor stream containing a majority of oxygenates in the oxygenate feed and a liquid stream containing a majority of metalloaluminophosphate molecular sieve contaminants in the oxygenate feed;
   b) separating the vapor stream from the liquid stream;
   c) contacting the separated vapor stream with metalloaluminophosphate molecular sieve to convert the oxygenates in the stream to olefin product; and
   d) discarding at least a portion of the separated liquid steam, which contains metalloaluminophosphate molecular sieve catalyst contaminants,
wherein the metalloaluminophosphate molecular sieve catalyst contaminants in the discarded portion comprise at least one metal selected from the group consisting of iron, sodium, and potassium.

2. The process of claim 1, wherein the vapor stream contacting the metalloaluminophosphate molecular sieve contains at least 75 wt % of the oxygenates in the oxygenate feed.

3. The process of claim 2, wherein the vapor stream contacting the metalloaluminophosphate molecular sieve contains at least 85 wt % of the oxygenates in the oxygenate feed.

4. The process of claim 3, wherein the vapor stream contacting the metalloaluminophosphate molecular sieve contains at least 95 wt % of the oxygenates in the oxygenate feed.

5. The process of claim 4, wherein the vapor stream contacting the metalloaluminophosphate molecular sieve contains at least 98 wt % of the oxygenates in the oxygenate feed.

6. The process of claim 1, wherein the oxygenate feed comprises methanol.

7. The process of claim 1, wherein at least a portion of the liquid stream is discarded and the discarded portion contains at least 75 wt % of the metalloaluminophosphate molecular sieve contaminants in the oxygenate feed.

8. The process of claim 7, wherein the discarded portion contains at least 80 wt % of the metalloaluminophosphate molecular sieve contaminants in the oxygenate feed.

9. The process of claim 8, wherein the discarded portion contains at least 85 wt % of the metalloaluminophosphate molecular sieve contaminants in the oxygenate feed.

10. The process of claim 9, wherein the discarded portion contains at least 90 wt % of the metalloaluminophosphate molecular sieve contaminants in the oxygenate feed.

11. The process of claim 1, wherein the metalloaluminophosphate molecular sieve contaminants are non-volatiles or partial volatiles.

12. The process of claim 1, wherein the oxygenate feed is heated to a temperature that is greater than or equal to the boiling point of methanol at the pressure at which the oxygenate feed is heated.

13. The process of claim 1, wherein the oxygenate feed is heated to a temperature that is lower than the boiling point of 1-octene at the pressure at which the oxygenate feed is heated.

14. The process of claim 1, wherein the oxygenate feed is heated to form a vapor stream at a temperature that is not greater than 200° C.

15. The process of claim 14, wherein the oxygenate feed is heated to form a vapor stream at a temperature that is not greater than 150° C.

16. The process of claim 1, wherein the discarded portion has a total iron, sodium and potassium concentration of at least 1 wppm, based on total weight of the liquid stream.

17. The process of claim 16, wherein the discarded portion has a total iron, sodium and potassium concentration of at least 5 wppm, based on total weight of the liquid stream.

18. The process of claim 17, wherein the discarded portion has a total iron, sodium and potassium concentration of at least 10 wppm, based on total weight of the liquid stream.

19. The process of claim 1, wherein the vapor stream contacting the metalloaluminophosphate molecular sieve contains not greater than 5 wppm of any one metal selected from the group consisting of iron, sodium and potassium, based on total weight of the vapor stream contacting the sieve.

20. The process of claim 19, wherein the vapor stream contacting the metalloaluminophosphate molecular sieve contains not greater than 2 wppm of any one metal selected from the group consisting of iron, sodium and potassium, based on total weight of the vapor stream contacting the sieve.

21. The process of claim 20, wherein the vapor stream contacting the metalloaluminophosphate molecular sieve contains not greater than 1 wppm of any one metal selected from the group consisting of iron, sodium and potassium, based on total weight of the vapor stream contacting the sieve.

22. The process of claim 21, wherein the vapor stream contacting the metalloaluminophosphate molecular sieve contains not greater than 0.5 wppm of any one metal selected from the group consisting of iron, sodium and potassium, based on total weight of the vapor stream contacting the sieve.

23. The process of claim 1, wherein a majority of the oxygenate in the oxygenate feed is methanol.

24. The process of claim 1, wherein the steps of heating the oxygenate and separating the vapor stream are carried out in one stage.

25. The process of claim 1, wherein the steps of heating the oxygenate and separating the vapor stream are carried out in more than one stage.

26. A process for converting oxygenate feed to olefin product, comprising the steps of:
   a) heating an oxygenate feed comprising methanol and metalloaluminophosphate molecular sieve catalyst contaminants, at atmospheric pressure or above, to at least the boiling point of the methanol at the pressure at which the oxygenate feed is heated, to form a vapor stream containing a majority of the methanol in the oxygenate feed and a liquid stream containing a majority of metalloaluminophosphate molecular sieve contaminants in the oxygenate feed, wherein the metalloaluminophosphate molecular sieve catalyst contaminants in the liquid stream comprise at least one metal selected from the group consisting of iron, sodium, and potassium;

b) separating the vapor stream from the liquid stream, wherein the liquid stream comprises a majority of the metalloaluminophosphate molecular sieve catalyst contaminants in the oxygenate feed; and c) contacting the separated vapor stream with metalloaluminophosphate molecular sieve catalyst to convert the methanol in the vapor stream into olefin product.

27. The process of claim 26, wherein the process further comprises a step of discarding at least a portion of the separated liquid stream.

28. The process of claim 26, wherein the steps of heating the oxygenate feed and separating the vapor stream are carried out in one stage.

29. The process of claim 28, wherein the steps of heating the oxygenate feed and separating the vapor stream are carried out in more than one stage.

30. The process of claim 26, wherein the vapor stream contacting the metalloaluminophosphate molecular sieve contains at least 75 wt % of the methanol in the oxygenate feed.

31. The process of claim 30, wherein the vapor stream contacting the metalloaluminophosphate molecular sieve contains at least 85 wt % of the methanol in the oxygenate feed.

32. The process of claim 31, wherein the vapor stream contacting the metalloaluminophosphate molecular sieve contains at least 95 wt % of the methanol in the oxygenate feed.

33. The process of claim 32, wherein the vapor stream contacting the metalloaluminophosphate molecular sieve contains at least 98 wt % of the methanol in the oxygenate feed.

34. The process of claim 26, wherein at least a portion of the liquid stream is discarded and the discarded portion contains at least 75 wt % of the metalloaluminophosphate molecular sieve contaminants in the oxygenate feed.

35. The process of claim 34, wherein the discarded portion contains at least 80 wt % of the metalloaluminophosphate molecular sieve contaminants in the oxygenate feed.

36. The process of claim 35, wherein the discarded portion contains at least 85 wt % of the metalloaluminophosphate molecular sieve contaminants in the oxygenate feed.

37. The process of claim 36, wherein the discarded portion contains at least 90 wt % of the metalloaluminophosphate molecular sieve contaminants in the oxygenate feed.

38. The process of claim 26, wherein the metalloaluminophosphate molecular sieve contaminants are non-volatiles or partial volatiles.

39. The process of claim 26, wherein the oxygenate feed is heated to a temperature that is lower than the boiling point of 1-octene at the pressure at which the oxygenate feed is heated.

40. The process of claim 26, wherein the oxygenate feed is heated to form a vapor stream at a temperature that is not greater than 200° C.

41. The process of claim 40, wherein the oxygenate feed is heated to form a vapor stream at a temperature that is not greater than 150° C.

42. The process of claim 26, wherein the discarded portion has a total iron, sodium and potassium concentration of at least 1 wppm, based on total weight of the liquid stream.

43. The process of claim 42, wherein the discarded portion has a total iron, sodium and potassium concentration of at least 5 wppm, based on total weight of the liquid stream.

44. The process of claim 43, wherein the discarded portion has a total iron, sodium and potassium concentration of at least 10 wppm, based on total weight of the liquid stream.

45. The process of claim 26, wherein the vapor stream contacting the metalloaluminophosphate molecular sieve contains not greater than 5 wppm of any one metal selected from the group consisting of iron, sodium and potassium, based on total weight of the vapor stream contacting the sieve.

46. The process of claim 45, wherein the vapor stream contacting the metalloaluminophosphate molecular sieve contains not greater than 2 wppm of any one metal selected from the group consisting of iron, sodium and potassium, based on total weight of the vapor stream contacting the sieve.

47. The process of claim 46, wherein the vapor stream contacting the metalloaluminophosphate molecular sieve contains not greater than 1 wppm of any one metal selected from the group consisting of iron, sodium and potassium, based on total weight of the vapor stream contacting the sieve.

48. The process of claim 47, wherein the vapor stream contacting the metalloaluminophosphate molecular sieve contains not greater than 0.5 wppm of any one metal selected from the group consisting of iron, sodium and potassium, based on total weight of the vapor stream contacting the sieve.

49. The process of claim 26, wherein the process further comprises a step of discarding at least a portion of the separated liquid stream.

50. A process for forming an olefin product, comprising the steps of:
   a) contacting a synthesis gas with a carbon oxide conversion catalyst to form a feedstream that comprises methanol;
   b) transporting the feedstream in a container to a location geographically distinct from that where the feedstream was formed;
   c) heating the transported feedstream to form a vapor stream that comprises a majority of methanol in the feedstream and a liquid stream that contains metalloaluminophosphate molecular sieve contaminants, wherein the metalloaluminophosphate molecular sieve catalyst contaminants comprise at least one metal selected from the group consisting of iron, sodium and potassium;
   d) separating the vapor stream from the liquid stream; and
   e) contacting the separated vapor stream with metalloaluminophosphate molecular sieve to convert the methanol in the feedstream to olefin product.

51. The process of claim 50, wherein the vapor stream contacting the metalloaluminophosphate molecular sieve contains at least 75 wt % of the methanol in the feedstream.

52. The process of claim 51, wherein the vapor stream contacting the metalloaluminophosphate molecular sieve contains at least 85 wt % of the methanol in the feedstream.

53. The process of claim 52, wherein the vapor stream contacting the metalloaluminophosphate molecular sieve contains at least 95 wt % of the methanol in the feedstream.

54. The process of claim 53, wherein the vapor stream contacting the metalloaluminophosphate molecular sieve contains at least 98 wt % of the methanol in the feedstream.

55. The process of claim 54, wherein at least a portion of the separated liquid stream is discarded and the discarded portion contains at least 75 wt % of the metalloaluminophosphate molecular sieve contaminants in the transported feedstream.

56. The process of claim 55, wherein the discarded portion contains at least 80 wt % of the metalloaluminophosphate molecular sieve contaminants in the transported feedstream.

57. The process of claim 56, wherein the discarded portion contains at least 85 wt % of the metalloaluminophosphate molecular sieve contaminants in the transported feedstream.

58. The process of claim 57, wherein the discarded portion contains at least 90 wt % of the metalloaluminophosphate molecular sieve contaminants in the transported feedstream.

59. The process of claim 50, wherein the metalloaluminophosphate molecular sieve contaminants are non-volatiles or partial volatiles.

60. The process of claim 50, wherein the transported feedstream is heated to a temperature that is greater than or equal to the boiling point of methanol at the pressure at which the oxygenate feed is heated.

61. The process of claim 50, wherein the transported feedstream is heated to a temperature that is lower than the boiling point of 1-octene at the pressure at which the oxygenate feed is heated.

62. The process of claim 50, wherein the transported feedstream is heated to form a vapor stream at a temperature that is not greater than 200° C.

63. The process of claim 62, wherein the transported feedstream is heated to form a vapor stream at a temperature that is not greater than 150° C.

64. The process of claim 50, wherein at least a portion of the liquid stream is discarded and the discarded portion has a total iron, sodium and potassium concentration of at least 1 wppm, based on total weight of the discarded portion.

65. The process of claim 64, wherein the discarded portion has a total iron, sodium and potassium concentration of at least 5 wppm, based on total weight of the discarded portion.

66. The process of claim 65, wherein the discarded portion has a total iron, sodium and potassium concentration of at least 10 wppm, based on total weight of the discarded portion.

67. The process of claim 50, wherein the vapor stream contacting the metalloaluminophosphate molecular sieve contains not greater than 5 wppm of any one metal selected from the group consisting of iron, sodium and potassium, based on total weight of the vapor stream contacting the sieve.

68. The process of claim 67, wherein the vapor stream contacting the metalloaluminophosphate molecular sieve contains not greater than 2 wppm of any one metal selected from the group consisting of iron, sodium and potassium, based on total weight of the vapor stream contacting the sieve.

69. The process of claim 68, wherein the vapor stream contacting the metalloaluminophosphate molecular sieve contains not greater than 1 wppm of any one metal selected from the group consisting of iron, sodium and potassium, based on total weight of the vapor stream contacting the sieve.

70. The process of claim 69, wherein the vapor stream contacting the metalloaluminophosphate molecular sieve contains not greater than 0.5 wppm of any one metal selected from the group consisting of iron, sodium and potassium, based on total weight of the vapor stream contacting the sieve.

71. The process of claim 50, wherein the process further comprises a step of discarding at least a portion of the separated liquid stream.

72. The process of claim 50, wherein the steps of heating the transported feedstream and separating the vapor stream are carried out in one stage.

73. The process of claim 50, wherein the steps of heating the transported feedstream and separating the vapor stream are carried out in more than one stage.

74. The process of claim 1, further comprising the step of polymerizing the olefin product to make an olefin polymer product.

75. The process of claim 26, further comprising the step of polymerizing the olefin product to make an olefin polymer product.

76. The process of claim 50, further comprising the step of polymerizing the olefin product to make an olefin polymer product.

* * * * *